US007718385B2

(12) United States Patent
Dick

(10) Patent No.: US 7,718,385 B2
(45) Date of Patent: May 18, 2010

(54) BIOACTIVATION OF ALKYLATING AGENTS FOR CANCER TREATMENT

(75) Inventor: Ryan A. Dick, Berkeley, CA (US)

(73) Assignee: The Johns Hopkins University, Baltimore, MD (US)

( * ) Notice: Subject to any disclaimer, the term of this patent is extended or adjusted under 35 U.S.C. 154(b) by 450 days.

(21) Appl. No.: 10/968,727

(22) Filed: Oct. 18, 2004

(65) Prior Publication Data

US 2005/0176074 A1 Aug. 11, 2005

Related U.S. Application Data

(60) Provisional application No. 60/512,350, filed on Oct. 17, 2003, provisional application No. 60/605,256, filed on Aug. 27, 2004.

(51) Int. Cl.
*G01N 33/574* (2006.01)
(52) U.S. Cl. ..................... 435/7.23; 560/115; 564/17; 564/57
(58) Field of Classification Search ................ None
See application file for complete search history.

(56) References Cited

U.S. PATENT DOCUMENTS

| | | | |
|---|---|---|---|
| 5,723,632 A | 3/1998 | McMorris | |
| 5,932,553 A | 8/1999 | McMorris et al. | |
| 6,025,328 A | 2/2000 | McMorris et al. | |
| 6,469,184 B1 | 10/2002 | McMorris | |
| 6,548,679 B1 | 4/2003 | McMorris et al. | |

OTHER PUBLICATIONS

McMorris et al. (Drug Metabolism and Disposition 1999; 27: 983-985).*
McMorris et al. (J. Natural Products 1996; 59: 896-899).*
McMorris et al. (Biochemical Pharmacology 1999; 57: 83-88).*
McMorris et al. (J. Org. Chem. 2001; 66: 6158-6163).*
Freshney (Culture of Animal Cells, A Manual of Basic Technique, Alan R. Liss, Inc., 1983, New York, p. 4).*
Dermer (Bio/Technology, 1994, 12:320).*
Babiychuk, E., Kushnir, S., Belles-Boix, E., Van Montagu, M.., and Inze, D. (1995) *J Biol Chem* 270, 26224-31.
Baillie, T. A. and Kassahun, K. Biological reactive intermediate in drug discovery and development: a perspective from the pharmaceutical industry, Adv Exp Med Biol. 500: 45-51, 2001.
Bayes, M., Rabasseda, X., and Prous, J. R. Gateways to clinical trials. Mar. 2003, Methods Find Exp Clin Pharmacol. 25: 145-68, 2003.
Blattner, F.R., Plunkett, G., 3rd, Bloch, C.A., Perna, N.T., Burland, V., Riley, M., Collado-Vides, J., Glasner, J.D., Rode, C.K., Mayhew, G.F., Gregor, J., Davis, N.W., Kirkpatrick, H.A., Goeden, M.A., Rose, D.J., Mau, B., and Shao, Y. (1997) *Science* 277, 1453-74.
Britten, C. D., Hilsenbeck, S. G., Eckhardt, S. G., Marty, J., Mangold, G., MacDonald, J. R., Rowinsky, E. K., Von Hoff, D. D., and Weitman, S. Enhanced antitumor activity of 6-hydroxymethylacylfulvene in combination with irinotecan and 5-fluorouracil in the HT29 human colon tumor xenograft model, Cancer Res. 59: 1049-53, 1999.
Carmichael, J., DeGraff, W. G., Gazdar, A. F., Minna, J. D., and Mitchell, J. B. Evaluation of a tetrazolium-based semiautomated colorimetric assay: assessment of chemosensitivity testing, Cancer Res. 47: 936-42, 1987.
Clish, C.B., Levy, B.D., Chiang, N., Tai, H.H., and Serhan, C.N. (2000), *J Biol Chem* 275,25372-80.
Dick, R. A., Kwak, M. K., Sutter, T. R., and Kensler, T. W. Antioxidative function and substrate specificity of NAD(P)H-dependent alkenal/one oxidoreductase. A new role for leukotriene $B_4$ 12-hydroxydehydrogenase/15oxoprostaglandin 13-reductase, J Biol Chem. 276: 40803-10, 2001.
Dick, R.A., Yu, X., and Kensler, T.W., *Clinical Cancer Research*, vol. 10, 1492-1499, Feb. 15, 2004.
Eder, E., Hoffman, C., and Deininger, C. (1991), *Chem Res Toxicol* 4, 50-57.
Edwards, K.J., Barton, J.D., Rossjohn, J., Thorn, J.M., Taylor, G.L., and Ollis, D.L. (1996) *Arch Biochem Biophys* 328, 173-83.
Ensor, C.M., Zhang, H., and Tai, H.H. (1998), *Biochem J* 330, 103-8.
Esterbauer, H., Schaur, .R..J., and Zollner, H. (1991), *Free Radic Bio Med* 11, 81-128.
Fillgrove, K.L., and Anderson, V.E. (2001) *Biochemistry* 40, 12412-21.
Fromm, H.J. (1983) in *Contemporary enzyme kinetics and mechanism* (Purich, D. L., ed), pp. 233-251, Academic Press, New York.
Groman, E.V., Schultz, R.M., Engel, L.L., and Orr, J.C. (1976) *Eur J Biochem* 63, 427-9.
Gunzburg, W.H., Lohr, M., and Salmons, B. (2002) *Expert Opin. Investig. Drugs* 11(6), 1-18.
Haynes, R.L., Szweda, L., Pickin, K., Welker, M.E., and Townsend, A.J. (2000), *Mol. Pharmacol* 58, 788-94.
Hirata, T., Tamura, Y., Yokobatake, N., Shimoda, K., and Ashida, Y. (2000) *Phytochemistry* 55, 297-303.
Kelner, M. J., McMorris, T. C., Montoya, M. A., Estes, L., Rutherford, M., Samson, K. M., and Taetle, R. Characterization of cellular accumulation and toxicity of illudin S in sensitive and nonsensitive tumor cells, Cancer Chemother Pharmacol. 40: 65-71, 1997.
Kelner, M. J., McMorris, T. C., and Taetle, R. Preclinical evaluation of illudins as anticancer agents: basis for selective cytotoxicity, J Natl Cancer Inst. 82: 1562-5, 1990.
Kelner; M: J., McMorris, T.. C., Beck, W. T., Zamora, J. M., and Taetle, R. Preclinical evaluation of illudins as anticancer agents, Cancer Res. 47: 3186-9, 1987.
Leggas, M., Stewart, C. F., Woo, M. H., Fouladi, M., Cheshire, P. J., Peterson, J. K., Friedman, I-I. S., Billups, C., and Houghton, P. J. Relation between Irofulven (MGI-114) systemic exposure and tumor response in human solid tumor xenografts, Clin Cancer Res. 8: 3000-7, 2002.

(Continued)

*Primary Examiner*—Brandon J Fetterolf
(74) *Attorney, Agent, or Firm*—Edwards Angell Palmer & Dodge LLP; Peter F. Corless; Jonathan M. Sparks

(57) ABSTRACT

A rapid screening method for identifying acylfulvenes and acylfulvene analogs with improved chemotherapeutic properties has been developed. The mechanism of toxicity of irofulven, a potentially clinically useful member of the acylfulvene class, has been elucidated and provides guidance for design and testing of a new class of alkylating agents with structures related to irofulven. The role of alkenal/one oxidoreductase (AOR) is shown to be important in cancer cell susceptibility to this class of alkylating agent.

12 Claims, 5 Drawing Sheets

OTHER PUBLICATIONS

Lilley, P.E., Stamford, N.P., Vasudevan, S.G., and Dixon, N.E. (1993) *Gene* 129, 9-16.

MacDonald, J. R., Muscoplat, C. C., Dexter, D. L., .Mangold, G. L., Chen, S. F., Kelner, M. J., McMorris; T. C.,. and Von.. Hoff, D. D. Pre clinical antitumor activity of 6-hydroxymethylacylfulvene, a semisynthetic derivative of the mushroom toxin illudin S, Cancer Res. 57: 279-83, 1997.

Mano, J., Babiychuk, E., Belles-Boix, E., Hiratake, J., Kimura, A., Inze, D., Kushnir, S., and Asada, K. (2000) *Eur J Biochem* 267, 3661-71.

Mano, J., Torii, Y., Hayashi, S., Takimoto, K., Matsui, K., Nakamura, K., Inze, D., Babiychuk, E., Kushnir, S., and Asada, K. (2002) *Plant Cell Physiol* 43, 1445-55.

McMorris, T.C., Kelner, M.J., Wang, W., Yu, J., Estes, L.A., and Taetle, R. (Hydroxymethyl)acylfulvene: an illudin derivative with superior antitumor properties; J: Nat Prod. 59 896-9, 1996.

McMorris, T. C. and Anchel, M. Fungal: Metabolites. The Structures of the Novel Sesquiterpenoids Illudin-S and -M, J. Am. Chem. Soc. 87: 1594-1600, 1965.

McMorris, T. C., Elayadi, A. N., Yu, J., Hu, Y., and Kelner, M. J. Metabolism of antitumor hydroxymethylacylfulvene by rat liver cytosol, Drug Metab Dispos. 27: 983-5, 1999.

McMorris, T. C., Kelner, M.J., Wang, W., Moon, S., and Taetle, R. On the mechanism of toxicity of illudins: the role of glutathione, Chem Res Toxicol. 3: 574-9, 1990.

Nordling, E., Jornvall, H., and Persson, B. (2002) *Eur J Biochem*, 269, 4267-76.

Orr, G.A., and Blanchard, J.S. (1984) *Anal Biochem* 142, 232-4.

Persson, B., Zigler, J.S., Jr., and Jornvall, H. (1994) *Eur J Biochem* 226, 15-22.

Pocker, Y. (2001) *Chem Biol Interact* 130-132, 383-93.

Powis, G. Anticancer drugs: reactive metabolism and drug interactions, 1st edition, p. 444. Oxford, England: Pergamon Press, 1994.

Pratt, W. B. The anticancer drugs, $2^{nd}$ edition, p. 352. New York: Oxford University Press, 1994.

Primiano, T., Gastel, J.A., Kensler, T.W., and Sutter, T.R. (1996), Carcinogenesis 17, 2297-303.

Rao, P.V., Krishna, C.M., and Zigler, J.S., Jr. (1992) *J Biol Chem* 267, 96-102.

Remington's Pharmaceutical Sciences, $15^{th}$ Edition, Mack Publishing Co., 1975.

Rudolph, F.B. (1983) in *Contemporary enzyme kinetics and mechanism* (Purich, D.L., ed), pp. 207-232, Academic Press, New York.

Salanoubat, M., Genin, S., Artiguenave, F., Gouzy, J., Mangenot, S., Arlat, M., Billault, A., Brottier, P., Camus, J.C., Cattolico, L., Chandler, M., Choisne, N., Claudel-Renard, C., Cunnac, S., Demange, N., Gaspin, C., Lavie, M., Moisan, A., Robert, C., Saurin, W., Schiex, T., Siguier, P., Thebault, P., Whalen, M., Wincker, P., Levy, M., Weissenbach, J., and Boucher, C.A. (2002) *Nature* 415, 497-502.

Sato, Y., Kashimoto,.S., MacDonald, J. R., and.Nakano, K. In vivo antitumour efficacy of MGI-114 (6-hydroxymethylacylfulvene, HMAF) in various human tumour xenograft models including several lung and gastric tumours, Eur J Cancer. 37:1419-28, 2001.

Sekhar, V.C., and Plapp, B.V. (1988) Biochemistry 27, 5082-8.

Tanaka, K., Inoue, T., Kadota, S., and Kikuchi, T. Metabolism of illudin S, a toxic principle of *Lampteromyces japonicus*, by rat liver. 1. Isolation and identification of cyclopropane ring- cleavage metabolites, Xenobiotica. 20:671-681, 1990.

Tanaka, K., Inoue, T., Kadota, S., and Kikuchi, T. Metabolism by rat liver cytosol of illudin S, a toxic substance of *Lampteromyces japonicus*; II. Characterizationof illudin S-metabolizing enzymes Xenobiotica. 22: 33-39, 1992.

Thorn, J.M., Barton, J.D., Dixon, N.E., Ollis, D.L., and Edwards, K.J. (1995) *J Mol Biol* 249, 785-99.

Uchida, K. (2000) *Mech Ageing Dev*, 116, 135-40.

Wratten, C.C., and Cleland, W.W. (1963) *Biochemistry* 2, 935-941.

Yokomizo, T., Izumi, T., Takahashi, T., Kasama, T., Kobayashi, Y., Sato, F., Taketani, Y., and Shimizu, T., (1993), *J. Biol Chem* 268, 18128-35.

Yokomizo, T., Ogawa, Y., Uozumi, N., Kume, K., Izumi, T., and Shimizu, T. cDNA cloning, expression, and mutagenesis study of leukotriene $B_4$ hydroxydehydrogenase, J Biol Chem 271: 2844-50, 1996.

Zheng, R., and Blanchard, J.S. (2000) *Biochemistry* 39, 3708-17.

* cited by examiner

1 R=H  Illudin M
2 R=OH Illudin S

7 Irofulven

3 $R_1$=H;  $R_2$=OH
4 $R_1$=H;  $R_2$=Cl
5 $R_1$=OH; $R_2$=OH
6 $R_1$=OH; $R_2$=Cl

8

BIOACTIVATION OF ALKYLATING AGENTS FOR CANCER TREATMENT

RELATED APPLICATIONS

This application claims benefit of U.S. Provisional Patent Applications Ser. No. 60/512,350 filed Oct. 17, 2003, and application Ser. No. 60/605,256 filed Aug. 27, 2004, the entire contents of which are incorporated herein by reference in their entirety.

This invention was supported in part by a Grant No. CA 39416 and CA 09243 from the National Institutes of Health. The United States Government has certain rights in the invention.

BACKGROUND OF THE INVENTION

1. Field of the Invention

The present invention relates to the field of medical arts; more particularly to methods of determining cancer cell sensitivity to acylfulvene class alkylating agents and to insights for design and identification of anticancer alkylating prodrugs.

2. Background

Cancer is second only to heart disease as a leading cause of death in the United States. Cancer occurs when cells continue to divide and fail to die at the appropriate time. Under normal circumstances, the many types of cells that make up the body grow and divide to produce more cells as they are needed in order to maintain a healthy state. Despite notable success in cancer treatments, current therapies have not yet significantly affected mortality rates for some of the more common cancers. The most common therapies include radiation and drug treatments, often used in combination. At present there are only a relatively small number of clinically active anti-cancer compounds, many of which have limited activity and/or are toxic to healthy cells.

Alkylating agents are a class of such drugs that trigger cell death by covalently binding to cellular nucleophiles such as DNA and proteins. Several alkylating agents, such as cyclophosphamide, ifosphamide and mytomycin C, are prodrugs that require metabolic activation to unmask inherent electrophilicity of an effective functional group. Selective toxicity to cancer cells is due to specific uptake of the activated metabolite (e.g., cyclophosphamide and ifosphamide) or by activation by an enzyme or by various substances in the cellular environment.

Alkylating agents exert their action by interacting with DNA, damaging the DNA so that it can no longer replicate, generally by DNA strand breakage or intra- or interstrand crosslinking of bases. Some agents may act by adding alkyl groups to DNA bases, formation of cross bridges between DNA molecules and inducing mutations arising from mispairing; however, agents causing mispairing are considered undesirable because this may lead to increased malignant proliferation (cancer). Types of alkylating agents include mustards, ethylenimes, alkylsulfonates, triazines, piperazines and nitrosureas. Cyclosporamide is used in cancer therapies and is thought to be selectively activated to some extent by cancer cells, so that they are relatively more toxic to cancer cells than to normal cells.

Illudins are natural products, first isolated from the toxic Jack O'Lantern mushroom. They were identified as candidates for new cancer agents (Kelner, et al., 1990) and used to further identify a sub-class of less toxic chemotherapeutics, the acylfulvenes (Kelner, et al. Cancer Chemotherapy and Pharmacology, 1999) of which 6-hydroxymethylacylfulvene (HMAF) was identified as a lead compound. Despite improved effectiveness over the illudins, it was recognized that little was known how the acylfulvenes work in the body and that identification of other more effective acylfulvene-related compounds was an important goal.

Many alkylating compounds have been tested for anticancer activity; however, most are unable to preferentially kill cancer cells. As noted, irofulven is a member of the acylfulvene class of compounds, which has performed well in tests of HT29 and MV522 induced tumors in mice (MacDonald, et al., 1997; Britten, et al., 1999. Although some clinical trials have been initiated, the toxicity of irofulven continues to be a major concern.

Irofulven is a semisynthetic derivative of the mycotoxin illudin S. The sesquiterpenes illudin S and illudin M are unique toxins produced by the bioluminescent Jack O'lantern mushroom *Omphalotus illudens* and related species. They are potent antibacterial and antitumor compounds. Illudin S exhibits cytotoxic and cytostatic properties at nanomolar concentrations in several human tumor cell lines in vitro (Kelner, et al., 1997). It is actively transported into cells where it is thought to form protein and DNA adducts (Kelner, et al., 1990). Adduct formation in turn leads to inhibition of DNA synthesis, single-stranded DNA breaks, cell cycle arrest, and onset of apoptosis.

Human tumor cells with various multiple drug resistance phenotypes are known to be as sensitive to illudin S as parental non-multiple drug resistant lines, thus indicating promise as anticancer agents. Unfortunately, substantial systemic toxicity was shown in animal models, raising serious concerns for use in cancer treatments (Kelner, et al., 1987). In a search for related compounds with greater therapeutic indices, irofulven was synthesized, proving to be nearly 2 orders of magnitude less cytotoxic than illudin S. While clearly a more promising candidate for cancer chemotherapy than illudin S, irofulven has similar drawbacks because of significant toxicity, including therapeutic levels that are close or overlap with toxicity levels. Many patients therefore cannot be treated with this drug due to myelosuppression and renal dysfunction.

HMAF is believed to act as an alkylating agent by forming DNA, RNA, and protein adducts that are preferentially cytotoxic to human cancer cells. Despite the conspicuous differences in cytotoxicity between illudin S and irofulven, it has long been assumed that the same molecular mechanism causes their cytotoxic effect (McMorris, et al., 1996). Studies of illudin and acylfulvene metabolites isolated from reactions with rat liver cytosol (Tanaka, et al., 1990; McMorris, et al., 1999) led to the suggestion that reduction of the carbon-carbon double bond of the $\alpha,\beta$-unsaturated ketone of an illudin or acylfulvene would lead to an extremely unstable electrophilic cyclohexadiene intermediate. Attack of the cyclopropyl group by a cellular nucleophile would then lead to adduct formation, dysfunction of the adducted macromolecule, and ultimately cell death. Although chlorinated and hydroxylated metabolites were isolated and thought to represent reaction of the putative electrophilic intermediate with chloride anion and water nucleophiles, respectively (Tanaka, et al., 1990), no adduct was directly observed.

The improved efficacy of HMAF over the parental illudins has led to attempts to develop second and third generation compounds that are less toxic, yet maintain cancer cell selectivity. Numerous acylfulvenes and illudin analogs have been prepared, including those disclosed in U.S. Pat. No. 6,025,328; U.S. Pat. No. 5,932,553; U.S. Pat. No. 6,548,679; each of which is herein incorporated by reference in its entirety. It is not known which, if any, of these analogs is less cytotoxic to normal cells than the parent irofulven.

Deficiencies in the Art

Despite the wide use of chemotherapy, there are several major drawbacks due to the chemical nature of some of these drugs. Ideally, cancer treatments will cure the cancer, but most chemotherapeutics control the disease for a limited amount of time before losing effectiveness. Exactly why this happens is not known; however, chemotherapy remains one of the most used and often effective methods of cancer treatment. An important tool in developing cancer drugs is an understanding of the mechanism of drug action against a cancer cell. This will be a key in identifying and developing chemotherapeutics that are highly toxic toward the cancer but relatively non-toxic toward non-cancerous cells.

Selection of lead compounds for testing as chemotherapeutic drug candidates is often a time-consuming and inexact process. Rapid screening tests to evaluate old and new generation drugs are needed; this is particularly important for compounds that have promise as therapeutics but are unacceptably toxic to normal, healthy cells. In particular, rapid in vitro tests are needed to evaluate potential efficacy of acylfulvenes that are being developed as second and third generation irofulven alkylating agents for cancer chemotherapy.

SUMMARY OF THE INVENTION

The present invention addresses some of the problems associated with understanding what determines the effectiveness of alkylating chemotherapeutics such as the illudins that have sesquiterpene-related structures and particularly irofulven, which has an acylfulvene structure. It was found that the level of a particular $\alpha,\beta$-unsaturated ketone reductase in cancer cells was significantly correlated with sensitivity of those cells to irofulven. Consequently, a method for assessing the susceptibility of a wide range of cancer cells to cytotoxins that are metabolized by NADPH alkenal/one oxidoreductase (AOR) class enzymes has been developed. The invention further provides insights for designing structures that have increased efficacy as alkylating agents in cancer cells that have high-activity levels of AOR.

The insight provided into the mechanism by which AOR determines sensitivity of cancer cells to chemotherapeutic alkylating agents is important. The invention illustrates the importance in considering two factors: first, that prodrugs with certain structural features are reduced by AOR to form reactive metobilites; and, second, that cancer cells having higher activity levels of AOR are more susceptible to acylfulvene class drugs, particularly irofulven.

In one aspect of the invention, methods are provided for predicting cancer cell toxicity of a candidate acylfulvene drug by comparing the 8,9-unsaturated double bond reduction rate by AOR with the reduction rate of the 8,9-unsaturated ketone double bond of illudin M, illudin S or irofulven. A rate of reduction for an acylfulvene candidate drug on the order of one magnitude less than the reduction rate for illudin M or illudin S indicates that the acylfulvene will have cytotoxicity comparable to irofulven. The AOR reduction rate of irofulven appears to correlate with its toxicity relative to the illudins, having a cytotoxicity two orders of magnitude less than the illudins. The illudins are far too toxic to normal cells to be useful in human therapy.

A closely related aspect of the invention is a method to determine the sensitivity of a selected cancer cell to an acylfulvene class drug. The method comprises measuring the activity of AOR in a selected cancer cell, then comparing the level of activity to AOR activities in a standard cancer cell panel. The selected cancer cell may be from a cancer patient biopsy, or from a similar cancer obtained from another subject or cell collection. It is then possible to predict how effective treatment for this type of cancer will be when irofulven or other AOR sensitive alkylating agents are contemplated for treatments. In a typical scenario, the skilled practitioner may compare in vitro results of irofulven against a standard panel of cancer cells with similar levels of AOR activity. If the biopsied cancer cell has AOR levels equal to or higher than those cells susceptible to irofulven, there is a good probability of effective treatment with irofulven. Also to be considered will be irofulven analogs, which have been compared with irofulven for $\alpha,\beta$-unsaturated ketone reduction rates. This also provides the physician with options for using irofulven analogs rather than irofulven itself.

In a practical aspect therefore, the present invention provides an in vitro method of predicting in vivo cancer cell toxicity of an acylfulvene candidate drug. Such candidate drugs will have a close structural relationship to irofulven, at least to the extent of having an $\alpha,\beta$-unsaturated ketone or aldehyde double bond conjugated to another double bond and in communication with a group such as a cyclopropane that upon reduction of the double bond will form a reactive electrophilic moiety.

The candidate drug is incubated with a medium chain reductase that reduces an $\alpha,\beta$-unsaturated aldehyde/ketone fulvene at ring position 8,9 of the acylfulvene. The reductase can be AOR, but for in vitro purposes, other related reductases may provide similar results, even if those reductases are not the predominant reductases in vivo. A reduction rate for the candidate acylfulvene drug can be readily determined, either as a general specific activity or more specific maximal reduction rate (Vmax). Measurement of the specific activity is rapid and will provide a preliminary screen of suitable candidate drugs. Calculation of Vmax permits determination of Km of the candidate, which is the concentration of substrate required for half-maximal activity (½×Vmax). Under normal conditions, Km is an indicator of the affinity of the enzyme for the drug. Drugs with lower Km values will require lower concentrations for activation by AOR, which translates to lower therapeutic doses and decreased side effects.

Once the candidate drug reduction rate is determined, whether by specific activity or Vmax, its rate is compared with the corresponding rate for a model or standard substrate, preferably irofulven. Comparisons may also be made with the illudins, such as illudin M and illudin S, or as more therapeutically acceptable acylfulvenes are identified, with the rate values for those compounds. A reduction rate for the candidate drug less than the reduction rate for the model substrate is to a certain extent predictive of increased in vivo cancer cell toxicity of the candidate acylfulvene drug compared with the model substrate. For example, where the model substrate is illudin M, a promising candidate will have a Vmax of about one order of magnitude less than illudin M; if the model substrate is illudin S, the candidate will have a Vmax of about two orders of magnitude less than illudin S; and if the model substrate is irofulven, the candidate will have a Vmax about the same or less than irofulven. Candidate drugs with Vmax values two orders of magnitude less than irofulven would not be considered as improved chemotherapeutic alkylating agents over the current standard model irofulven.

The reductase is preferably AOR, but may also be a reductase that is structurally and functionally similar, such as a polypeptide having the amino acid sequence of SEQ ID NO: 1, SEQ ID NO:3 or an amino acid sequence 40% to 99% identical, preferably at least 90% identical thereto. An exemplary AOR is encoded by a nucleic acid having the sequence of SEQ ID NO: 2, SEQ ID NO:4 or variants thereof including degenerate forms that encode the same polypeptides as SEQ ID NO: 1 or SEQ ID NO: 3.

Although unsaturated double bond stability toward reduction is indicated by Vmax reduction rates, stability can be further assessed by incubating a candidate acylfulvene drug with a nucleophile, such as glutathione. Rates of formation of the adducts provide a further indication of relatively stability of the α,β-unsaturated double bond and can be taken into consideration when assessing the candidate drug.

An aspect of the invention therefore is a method for optimizing selection of an acylfulvene or acylfulvene analog candidate drug. A first step is to determine the AOR Vmax reduction rate, or alternatively, the specific reduction rate of a candidate drug. This result will provide, by comparison with the reduction rate of irofulven, an additional assessment of the candidate drug reduction stability. This is then compared with a non-enzymatic reduction, which should confirm the stability characteristics of the double bond, at least with respect to the proposed mechanism of action for the acylfulvenes.

The candidate drug can be further evaluated by determining its TGI and/or GI50 growth rates in cells exposed to the drug. Preferably the growth rates of 293 cells are determined, in both the standard cell line and in 293 cells transformed to overexpress AOR. In optimizing selection and dosing of a candidate acylfulvene class compound, a reduction rate comparable to irofulven by both AOR and nonenzymatically, and a dose comparable to or less than required by irofulven for 100% or 50% growth inhibition (TGI or GI50) will provide the information necessary to optimize dosing once the candidate drug is identified as a potential therapeutic.

A related aspect of the invention is a method for predicting susceptibility of a cancer cell to irofulven, or to identified analogs of irofulven or acylfulvenes that show acceptable therapeutic activity. A first step is to cultivate a selected cancer cell. The cell may be one isolated from the body of a cancer patient or one from another source that is the same type of cancer. It is preferable to use the patient's cancer cells because of possible variation in even similar types of cancer. AOR activity of the selected cancer cell is then measured. This can be done quickly by measuring specific activity for an initial assessment to determine whether or not there is any significant AOR activity. The AOR activity for the selected cell is then compared with AOR activity of cancer cells in a standard cancer cell panel, which need only be those known to have an AOR activity range that brackets the AOR activity measured in the selected cancer cell. The susceptibility of each of the standard cells to irofulven, or other therapeutic acylfulvenes, is then used to predict effectiveness of irofulven against the selected cancer cell. This assessment is a rapid method of determining the suitability of irofulven for treatment of subjects with an identified cancer. Alternatively, AOR expression levels can be determined by a suitable immunoassay that utilizes AOR-specific antibodies.

A convenient source of standard cancer cells is the National Cancer Institute where a panel of 60 types of cancer cells and their growth rate susceptibility to irofulven is available. The cancer cells available include leukemia, non-small cell lung, colon, central nervous system, melanoma, ovarian, renal, prostate and breast cancer cells. The cells are further identified as particular cell lines, some of which include A549/ATCC, HOP-92, NCI-H460, HOP-62 for non-small cell lung; DU-145 prostate, HCC-2998 colon and T-47 breast.

The present invention can also provide a method of determining efficacy or dosage of irofulven required for cancer chemotherapy. A subject or patient in need of cancer therapy is identified and is considered for treatment with a chemotherapeutic agent. A biopsy sample is obtained. In the case of a leukemia a blood sample will be obtained. AOR activity is measured in the sample and this activity is compared to AOR activities in each of a standard panel of cancer cells. The cancer cells are preferably selected as those against which irofulven is effective. A good measure of this are the growth inhibition values determined at the National Cancer Institute (see Table 3) indicating that irofulven is effective against several cell lines of leukemia, non-small cell lung, colon, central nervous system and renal cancer cells. Irofulven treatment, if indicated, can be dose-adjusted up or down in accordance with irofulven efficacy against a cancer cell with comparable AOR activity.

The present invention also provides in vivo procedures designed to upregulate AOR production. It is believed that this may be accomplished by administering an expression vector that includes a gene encoding a polypeptide having the amino acid sequence of SEQ ID NO: 1 or sequences substantially identical thereto. This is expected to increase toxicity of irofulven or related analogs. Although AOR is likely to be upregulated in normal cells, it is believed that higher levels of AOR in cancer cells will make them relatively more susceptible to irofulven. This may be particularly advantageous when cancer cells are determined to have low levels of AOR, making them poor candidates for irofulven treatment.

Alternatively, AOR levels may be increased by administration of chemical inducers, including other enzymes such as glutathione-S-transferase, NAD(P)H:quinone reductase and superoxide reductase. Many naturally occurring and synthetic compounds are known to act as inducers for these phase 2/antioxidative enzymes, including several isothiocyanates and dithiolethiones. Diet may also have an effect since isothiocyanates are found in cruciferous vegetables such as broccoli and watercress. Phenylethylisothiocyanate has been administered to humans, and Oltipraz, a synthetic substituted dithiolethione approved for use in humans, has demonstrated efficacy in phase 2/antioxidative enzyme induction in humans.

Rather than administering an AOR gene directly, it should be feasible to culture cancer cells from a tissue biopsy, transform the cells ex vivo, then return the transformed cells to the subject so that overexpression of AOR in the transformed cells increases cytotoxicity of irofulven to the cancer cells. For solid tumors, the transformed cells can be provided directly into the tumor. For lymphomas and leukemias, it may be preferable to administer the transformed cells by injection, intravenously, IP or IM. It is believed that providing some cancer cells to either the tumor or the general circulation will cause provide levels of AOR in the neighborhood of the cancer cells, which will increase efficacy of irofulven and related alkylating chemotherapeutics.

DETAILED DESCRIPTION OF THE INVENTION

Figure 1:
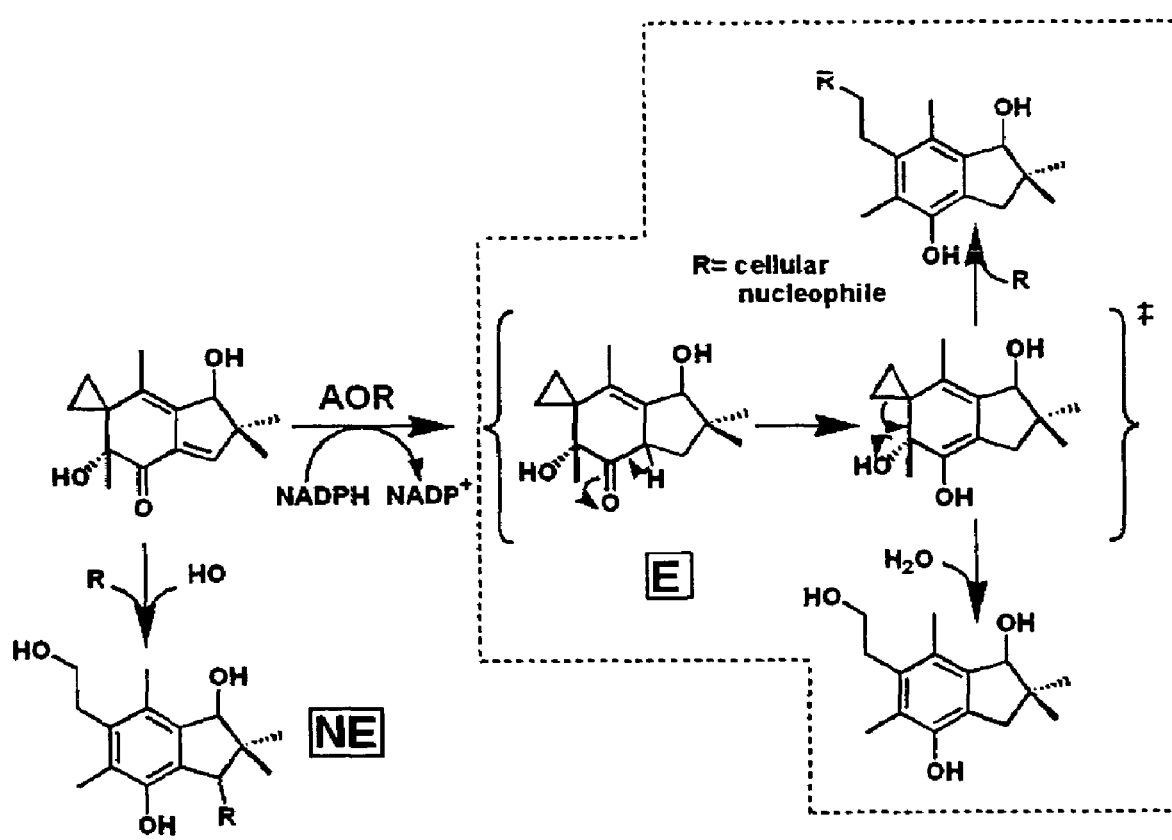
FIG. 1. Illudins and irofulven can react with nucleophiles nonenzymatically (NE) through addition to the 8,9-double bond or with the cyclopropyl group after enzymatic reduction (E) of the double bond.

The present invention has demonstrated that AOR levels in a cancer cell determine its susceptibility to the acylfulvene class of alkylating agents, which are of interest as chemotherapeutic agents. In vitro studies show that the acylfulvenes, particularly irofulven, are metabolized by AOR at least two times less rapidly than the related illudins and that the slower metabolism correlates with higher cytotoxicity against cancer cells that express AOR. Importantly, there is a strong correlation between growth inhibition of cancer cells treated with irofulven and AOR activity in the cancer cell.

In determining how irofulven exerts its toxic effects on cancer cells, rates of AOR reduction of the unsaturated double bonds of the illudins and a semisynthetic acylfulvene were undertaken. Recombinant AOR rapidly reduced the $\alpha,\beta$-double bonds of illudins S and M, but a far slower rate of reduction was found in irofulven. This indicated that illudin cytotoxicity is not dependent on enzymatic activation, and further indicated that the far slower reduction of the irofulven $\alpha,\beta$-double bond would involve a different mechanism for in vivo cytotoxicity. This was confirmed by measuring AOR activities in 60 human tumor cell lines and correlating the AOR activities with irofulven sensitivity. These results were surprising because heretofor the cytotoxicity mechanism for both the illudins and irofulven was believed to be the same. Equally surprising was the recognition that the level of expressed AOR activity in the cancer cells is a major determinant of their sensitivity to irofulven.

NADPH-Dependent Alkenal/One Oxidoreductase (AOR)

AOR from the rat is a phase2/antioxidative enzyme known to catalyze the reduction of the carbon-carbon double bond of $\alpha,\beta$-unsaturated aldehydes and ketones. It is also known for its leukotriene $B_4$ 12-hydroxydehydrogenase activity. AOR may have arisen from a primitive alcohol dehydrogenase. The ability to hydrogenate electrophilic and cytotoxic $\alpha,\beta$-unsaturated carbonyls would likely have provided a selective advantage to organisms challenged with these molecules, especially in persistent cases of oxidative stress.

Of the AOR substrates identified, several are common environmental pollutants (methyl vinyl ketone and acrolein) or products of lipid peroxidation (Leggas, et al, 2002; MacDonald, et al., 1997). The latter process involves reaction of oxygen free radicals with polyunsaturated fatty acids to form aliphatic $\alpha,\beta$-unsaturated aldehydes such as 4-hydroxy-2-nonenal (4HNE), 2-hexenal, and 2,4-decadienal (MacDonald, et al., 1997). These reactive molecules likely mediate many of the detrimental effects of oxidative stress. 4HNE is extremely cytotoxic, an abundant product of lipid peroxidation, and an excellent substrate of AOR (Dick, et al., 2001). Cells engineered to overexpress AOR are resistant to 4HNE-mediated cell death and protein adduct formation (Pratt, 1994) thus indicating an important physiological anti-oxidative role of the NADPH-dependent activity of AOR.

AOR reduces the carbon-carbon double bond of a variety of $\alpha,\beta$-unsaturated aldehydes and ketones (Pratt, 1994). It is co-regulated in the rat with a variety of phase 2 anti-oxidative enzymes, including NAD(P)H:quinone reductase, glutathione-S-transferases, and UDP-glucuronosyltransferases through the Keapl/Nrf2 signaling pathway (2). $\alpha,\beta$-unsaturated aldehydes and ketones are electrophilic and capable of reacting via a Michael-addition mechanism with important cellular nucleophiles, which in turn leads to macromolecular (protein, DNA) dysfunction and cell death. Because saturated carbonyls lack this reactive moiety they are often far less toxic. Thus, it has been suggested that hydrogenation of the $\alpha,\beta$-double bond by AOR results in detoxification (Dick, et al., 2001; Sato, et al., 2001) of otherwise toxic substrates.

Rat liver cytosol can reduce the 8,9 double bond of illudins and acylfulvenes (see FIG. 1E) (Tanaka, et al., 1990; Tanaka, et al., 1992); however, the identity of the responsible enzyme(s) and the role of metabolism in the toxicities of the illudins and acylfulvenes was not known. Based on several characteristics of this activity, including cofactor preference, cytosol localization, inhibitor, and pH profile (Tanaka, et al., 1992), the present work showed that the responsible enzyme was NADPH-dependent alkenal/one oxidoreductase (AOR). Recombinant rat liver AOR exhibited robust illudin and irofulven reductase activities, and the metabolites of illudin M and irofulven formed were identical to those previously reported (13, 14 Tanaka, et al., 1990; McMorris, et al., 1999).

It had been assumed previously that since illudins M and S, and irofulven share a core molecular structure, they must act in similar ways to kill cells. Studies aimed at determining the mechanism of illudin toxicity compared with the irofulven mechanism of toxicity showed that this was not true.

Figure 2:
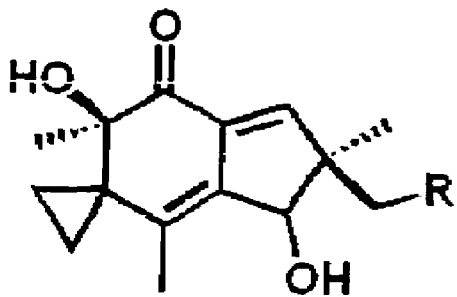
FIG. 2. Shows the molecular structures of illudin S, illudin M, irofulven and metabolites.
Figure 2:
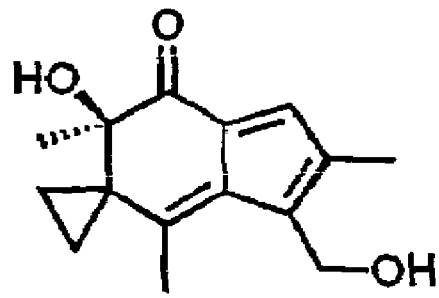
Figure 2:
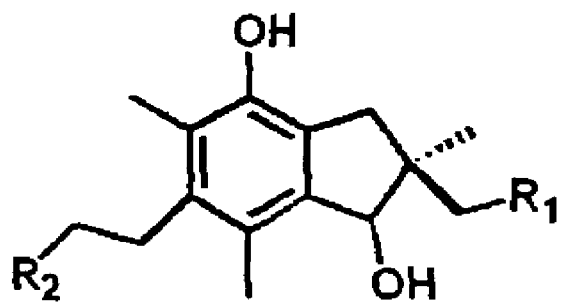
Figure 2:
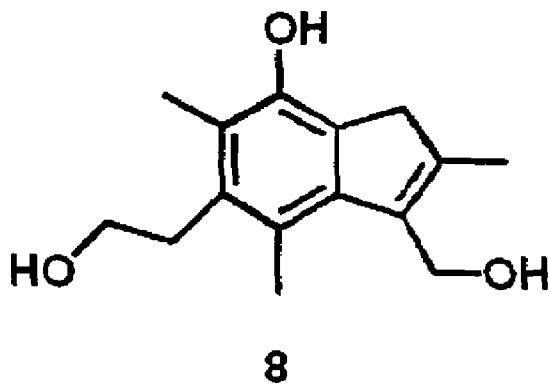

This core structure of illudins and acylfulvenes consists of an $\alpha,\beta$-unsaturated ketone that straddles a bicyclic ring system, a cyclopropyl group adjacent to a vinyl moiety, and an alcohol bearing carbon (FIG. 2, structures 1, 2, and 7). Upon reduction of the $\alpha,\beta$-double bond, intramolecular rearrangement generates an unstable cyclohexadiene intermediate that requires only opening of the strained cyclopropyl ring and expulsion of water to form a stable aromatic product. Several nucleophiles, including those found on DNA presumably, can attack and open this ring (FIG. 1). Depending on the kinetic stability of the intermediate, metabolism is either a detoxifying or activating process. If the intermediate is rapidly quenched by nucleophiles, such as hydroxide or chloride anions in the enzyme active site before it has the opportunity to react with important cellular nucleophiles (DNA or protein), metabolism by AOR will result in detoxification.

Alternatively, if the intermediate is stable enough to exist outside of the hydrophobic active site and reach important cellular nucleophiles, metabolism serves to activate the molecule. However reactivity of the 8,9-double adds an alternative route for adduct formation and toxicity (McMorris, et al., 1990). Many α,β-unsaturated carbonyl compounds are reactive electrophiles that spontaneously react with strong nucleophiles, including sulfhydryls and amines by a Michael-addition mechanism. If the 8,9-double bond is reactive enough to form adducts with important cellular nucleophiles, a nonenzymatic route of toxicity may predominate.

Figure 3A:
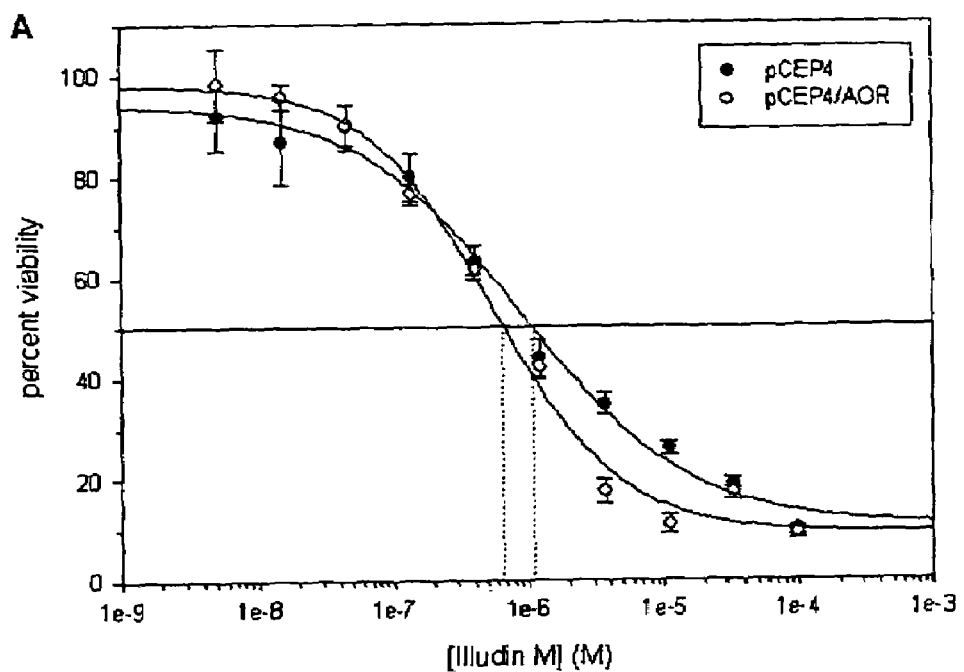
FIG. 3A. 293 cells were transfected with either a blank (pCEP4) or alkenal/one oxidoreductase (AOR) overexpression (pCEP4/AOR) vector and were challenged for 24 h with either illudin M. Cell viability was measured using a 96-well plate 3-(4,5-dimethylthiazol-2yl)-2,5-diphenyltetrazolium bromide assay. Each point represents data from eight determinations; experiments were done in triplicate; bars, ±SD.
Figure 3B:
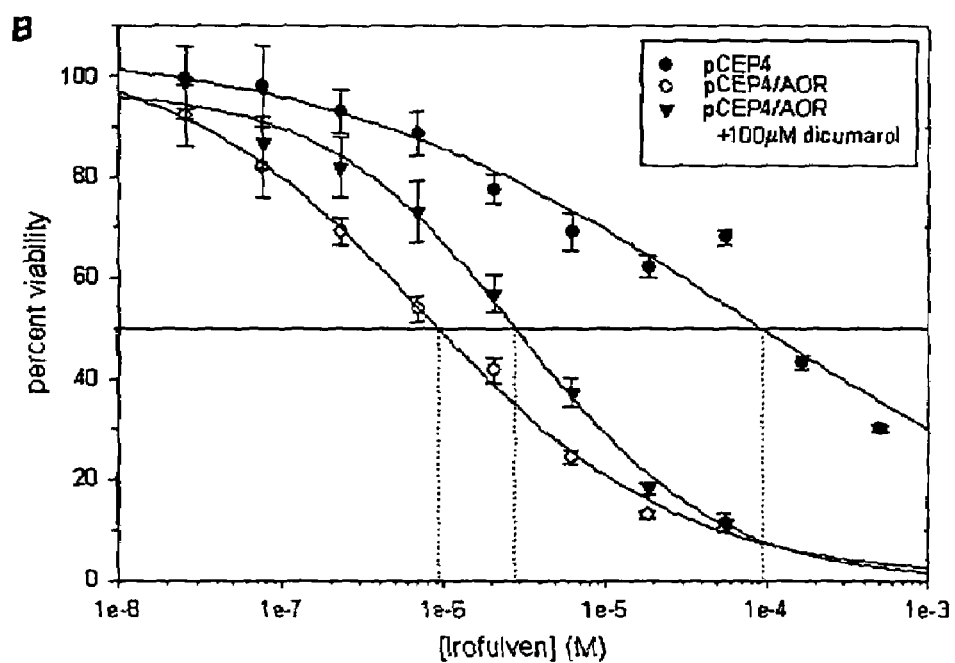
FIG. 3B. 293 cells were transfected as in FIG. 3A and challenged for 24 h with irofulven. Dicumarol is an AOR inhibitor. Cell viability was measured as in FIG. 3A.

The present invention provides data contradicting the assumption that irofulven is simply a less toxic analogue of illudin S and that the reaction pathways are identical. Metabolic reduction of the α,β-double bond of irofulven, but not illudin M or S, by AOR is an important determinant of toxicity. Human 293 cells engineered to overexpress AOR were at least 100-fold more sensitive to irofulven than control cells, whereas cells challenged with illudin M displayed no differential toxicity (FIG. 3A and FIG. 3B). Furthermore, using measurements of drug sensitivity made by the National Cancer Institute on a comprehensive panel of 58 human tumor cell lines, a strong positive association was observed with irofulven, but not illudin.

Irofulven

Irofulven is an anticancer chemotherapeutic and has been the subject of clinical phase studies in humans. It is an alkylating agent that forms DNA-protein adducts that are thought to be preferentially cytotoxic to human cancer cells. The present work has led to the discovery that irofulven is a prodrug that requires metabolic activation by AOR, an enzyme known to reduce the 8,9-double bonds of both illudins and acylfulvenes. The action of AOR on irofulven generates a reactive and electrophilic center around the cyclopropyl group.

Because both illudin M and irofulven are metabolized by AOR at reasonable rates and concentrations, the potential for metabolic activation in vivo exists. Evidence for illudin M activation by AOR using GSH trapping and LC/MS/MS detection shows that, unlike irofulven, illudin M also readily reacts about its α,β-double bond with thiol nucleophiles. In conjunction with the observation that most cells are sensitive to illudins at concentrations orders of magnitude below the $K_m$ values, it was concluded that cytotoxicity is mediated primarily by reaction through the 8,9-double bond.

Understanding the toxicity the acylfulvene class of compounds was an important step in determining the basis by which these compounds preferentially kill tumor cells. This work explains that the disparity between efficacies of the illudins and irofulven found in preclinical xenograft experiments is due to differential reactivities of the 8,9-double bonds. Illudin kills cells indiscriminately at very low concentrations due to the presence of an electrophilic α,β-unsaturated ketone. Activated irofulven appears to form adducts with a completely different set of macromolecules, which preferentially trigger apoptosis in cancer cells. Understanding the role of metabolism in the chemotherapeutic action of irofulven provides direction and guidance for design of more potent drugs for clinical evaluation.

Initially, efforts were focused on understanding AOR catalytic activity and particularly to investigate its reductase activity as a member of the medium-chain dehydrogenase/reductase family. Recombinant AOR and a 3-nonen-2-one substrate were used to perform steady-state initial velocity, product inhibition, and dead-end inhibition experiments, which elucidated an ordered Theorell-Chance kinetic mechanism with NADPH binding first and NADP+ leaving last.

Among other results, a nearly 20-fold preference for NADPH over NADH was observed. The dependence of kinetic parameters V and V/K on pH led to realization that a general acid with a pH of approximately 9.2 was involved.

Use of NADPH isomers stereospecifically labeled with deuterium at the 4-postion showed that AOR catalyzes the transfer of the pro-R hydride to the β-carbon of an α,β-unsaturated ketone, illudin M. Two-dimensional nuclear Overhauser effect NMR spectra then demonstrated that this atom becomes the R-hydrogen at this position on the metabolite.

Small primary kinetic isotope effects of 1.73 and 1.62 for V and V/K, respectively, were observed using [4R-$^2$H]NADPH suggested that hydride transfer was not rate limiting. Atomic absorption spectroscopy indicated absence of $Zn^{2+}$ from active preparations of AOR. It was concluded that AOR fits predictions made for medium-chain reductases and bears similar characteristics to well known medium-chain alcohol dehydrogenases.

The catalytic mechanism of AOR's predominant NADPH-dependent activity was investigated in a second stage of study. Steady-state kinetic experiments were performed to identify the kinetic mechanism. Solvent isotope effects and activity pKa's were calculated. Deuterium labeled NADPH was used to determine kinetic isotope effects and stereospecificity of hydride transfer. Finally, chelation agents and atomic absorption spectroscopy were used to probe for the presence of catalytic or structural $Zn^{2+}$.

A second electrophilic site, an α,β-unsaturated ketone, exists in each of the illudins and readily reacted, in the case of the illudins only (McMorris, et al., 1990), with reduced glutathione (GSH) and other sulfhydryl-containing species. An enzyme responsible for reduction of the α,β-double bond of illudin S had previously been partially characterized from rat liver cytosol (Tanaka, et al., 1992) and several of its characteristics were identical to those of rat NADPH-dependent alkenal/one oxidoreductase (AOR), including subcellular localization, cofactor preference, and inhibition profile (Dick, et al., 2001). AOR had been characterized previously as an inducible enzyme that catalyzes the detoxification of α,β-unsaturated lipid aldehydes formed during lipid peroxidation (Dick, et al., 2001).

In undertaking a study of AOR action on the illudins, it was postulated that metabolism via hydrogenation of the 8,9-double bonds of the illudins would unmask the electrophilicity that contributed to the toxic nature of the cyclopropyl moieties. Illudins S and M were rapidly metabolized by NAD(P)H-dependent alkenal/one oxidoreductase (AOR) with maximal rates of 115.9 and 44.1 micromoles $min^{-1}$ $mg^{-1}$ and $K_m$'s of 308 and 109 µM, respectively. Irofulven was reduced at a much slower rate: $V_{max}$ 275 nmoles $min_{-1}$ $mg_{-1}$ and $K_m$ 145 µM.

AOR is clearly important in the metabolism of the acylfulvene class drugs. Moreover, as seen in Table 2, some cancer cells have higher AOR activities and are considerably more sensitive to irofulven, which for convenience has been used as a model standard compound. It is expected that it will be possible to upregulate AOR either by gene therapy methods or by administration of an inducer. Although several inducers have been identified as co-regulators in rats at the transcriptional level, so far only isothiocyanates and dithiolethiones have demonstrated efficacy in humans. Isothiocyanates are natural products of cruciferous vegetables and have been administered in vegetable such as broccoli and watercress or in pure form; e.g., phenethyl isothiocyanate. Dithiolethiones are also products of cruciferous vegetables but are not produced at levels high enough for clinical utility. Oltipraz, a synthetic substituted dithiolethione, has been approved for use in humans and has shown efficacy in phase2/antioxidative enzyme induction in humans. Administration of either class of inducer would presumably upregulate AOR in the body, and possibly increase tumor sensitivity since tumors are more sensitive to irofulven adducts than normal tissue.

Gene therapy may also be used to increase AOR in the body, possibly to target cancer cells for transformation with an expression vector that includes a gene encoding AOR. An appropriate recombinant expression system may include those based on bacterial, yeast, insect or mammalian systems. Preferably a human AOR-encoding nucleic acid will be employed (SEQ ID NO: 4); however, other AOR may be used, such as rat AOR DNA (SEQ ID NO: 2) or other highly homologous AOR genes that will express hAOR (SEQ ID NO:3) or rat AOR (SEQ ID NO: 1) that is at least 40% identical to human AOL, preferably 70-80%, more preferably at least 85% identical and most preferably 90-100%. Targeting of the expression vectors can be achieved, for example, by retroviral vehicles that are designed to target to the cancer cells. For solid tumors, a large number of tumor cells could be transformed ex vivo, the injected into the tumor. Overexpression of AOR in these cells would attract metabolites of the cytotoxic prodrug to the tumor site, causing apoptosis not only of the transformed cells but also of neighboring cancer cells.

Alternatively, gene therapy vectors could be directed indiscriminately and include normal cells. It is believed that cancer cells are more sensitive to irofulven through covalent DNA bond formation or adducts than normal cells and may recover faster. It is evident that whatever the finer details of molecular trafficking, cancer cells with higher AOR activity metabolize higher amounts of irofulven, and presumably all structurally related molecules, and will die at lower drug concentrations.

Gene vector compositions are preferably dispersed in a pharmaceutically acceptable excipient or solution. Such compositions may be administered parenterally, intraperitoneally or, less likely, topically. Suitable injectable forms include sterile aqueous solutions or dispersions, all being in a pharmaceutically acceptable carrier, which includes any and all solvents, dispersion media and the like which are well-known in the art (see Remington's Pharmaceutical Sciences, 1975).

Cancer therapies may utilize more than one active agent. The screening system disclosed here need not be used only for screening single compounds. For example, other classes of anticancer agents such as inhibitors of DNA biosynthesis may in fact act in a synergistic manner with alkylating agents and may be tested as co-ingredients with irofulven or other acylfulvene. Examples include hydroxyurea, mercaptopurine, thioguanine, antibiotics such as daunorubicin and actinomycin D, mitotic disrupters such as taxol; and intercalating agents such as cisplatin. The expectation is that cocktails of drugs can be formulated that utilize far less drug than when either agent is used alone; and, by acting with different mechanisms may have a better chance to wipe out cancer cells that may be initially resistant to the alkylating chemotherapeutic agent.

Detection and measurement of AOR in vivo will be important as a predictor of sensitivity or resistance to prodrugs developed from the acylfulvenes or their analogs. This can be accomplished using, for example, irofulven as a model substrate for acylfulvene class drug candidates. AOR activity of the candidate compound and the standard model compound, preferably irofulven, in the presence of the cancer cells isolated from patient tumors or cancerous tissue can be determined by the kinetic measurements described herein. It may, in certain cases, be desirable to assess systemic activity of AOR. In such a case, a labeled substrate, for example, irofulven, could be administered. Labeled metabolites isolated from blood or urine could be analyzed for the metabolites resulting from the action of AOR.

It is important to recognize that the screening tests disclosed herein are compared and evaluated against a comparison standard. In the examples disclosed herein, irofulven is used because it has been clinically tested and its therapeutic index is well-known. Irofulven is an example of a standard for acylfulvenes because its metabolism and accordingly its toxicity, is different enough from that of illudin M to suggest value as a chemotherapeutic. Other standards for this type of screening test can also be developed and more precise systems for measuring kinetics in a standard assay may more closely identify numbers that are highly predictive of clinical results. It should also be possible to develop a therapeutic predictability index for this class of compounds so that a list of acylfulvene class of alkylating agents will allow selection for the type of cancer to be treated.

While the methods described have been applied to AOR activation of the anticancer prodrug irofulven, it should be apparent to one of skill in the art that the same principles may apply to other prodrugs that act as alkylating agents. Other enzymes may be involved in activation of prodrugs that affect DNA; for example, $\alpha,\beta$-reductases as well as homologs of AOR. Other classes of compounds outside the acylfulvenes may well be chemotherapeutic prodrugs that are activated by AOR.

Additionally, it is clear that there are structural requirements for AOR substrates; these include an activated $\alpha,\beta$-unsaturated bond such as an $\alpha,\beta$-unsaturated aldehyde or ketone but may possibly be activated by other geminal functional groups. Importantly, molecular stereochemistry of the prodrug is a factor because the reduction process must lead to an electrophilic intermediate that is stable enough to directly or indirectly interact with cellular DNA. Irofulven is currently the best model structure with a cleavable cyclopropane, but other spiro saturated rings might also be cleaved in a similar manner.

Figure 7:
FIG. 7. shows exemplary basic structure for compounds contemplated to be activated by AOR.

Based on the mechanistic studies disclosed herein, it is believed that the necessary structural characteristics include the $\alpha,\beta$-unsaturated double bond, which is reduced AOR, a cyclopropyl group whose electrophilic reactivity is unmasked by reduction by AOR, a hydroxyl group that serves as a leaving group and a cyclohexene ring that aromatizes when the saturated ketone ring tautomerizes, the cyclopropyl group opens and a water molecule molecule is eliminated. This basic structure is illustrated in FIG. 7 where R1 and R2 may include a large number of different substituents. R1 should have two characteristics: first, to decrease electron density at the $\alpha,\beta$-double bond in order to reduce the reactivity of that bond so that its reactivity is determined mainly by metabolic activation. Illudins are more reactive than irofulven because the irofulven double bond is stabilized through an extended $\pi$-bond network. There are a variety of electron withdrawing groups that could be substituted at the R1 position. As a second consideration, R1 is preferably hydrophobic and unbranched. Hydrophobicity at this position would be expected to drastically decrease the Km of the compound with respect to AOR whereas, based on previous studies, a bulky group would have the opposite effect. An exemplary R1 group is a phenyl with electron withdrawing substituents.

R2 is expected to be hydrophobic and unbranched. Dramatic increases in Km are exhibited in similar molecules substituted in this position. A decrease in Km indicates that at lower concentrations, more of the compound is metabolized and activated, presumably leading to decreased dosage requirements and fewer or decreased side effects. These are problems that currently plague irofulven.

Other classes of molecules can be tested against AOR, first to determine whether they are substrates for AOR; secondly to test them against a representative panel of cancer cells that have high AOR activity. Of course cell toxicity studies would also be required in order to assure that the test compounds are not unduly toxic to normal cells.

Materials and Methods

Abbreviations used are: AOR, NADPH-dependent alkenal/one oxidoreductase; 4HNE, 4-hydroxy-2-nonenal; MDR, medium-chain dehydrogenase/reductase; $LTB_4$, leukotriene $B_4$; LADH, liver alcohol dehydrogenase; 2D-NOESY, two-dimensional nuclear Overhauser effect NMR spectroscopy.

Materials: Chemicals and Reagents—Illudins M and S were supplied by the Developmental Therapeutics Program of the National Cancer Institute. Irofulven was synthesized from illudin S as described previously (8). It was purified using preparative TLC and flash chromatography and analyzed by $^1$H-NMR and electrospray-mass spectrometry. ESI-MS. Purity was estimated to be >95% by TLC. Recombinant rat AOR was expressed and purified as described by Dick, et al. (2001) (17).

GSH, NADPH, and all other chemicals were purchased from Sigma Aldrich (St. Louis, Mo.). trans-3-Nonen-2-one, trans-2-nonenal, and 2-nonanone were purchased from Aldrich. $D_2O$ ("100%"), ethanol-d6, methanol-$d^4$, and D-glucose-1-d were purchased from Cambridge Isotope Laboratories. All other chemicals and enzymes including glucose dehydrogenase from *Cryptococcus uniguttulatus* and alcohol dehydrogenase from *Thermoanaerobium brockii* were purchased from Sigma.

Kinetic Measurement of Metabolism of Illudins and Irofulven by AOR. Three similar assays were used to quantify rates of metabolism of illudins M and S, and irofulven. Varied concentrations of illudin M were added to a 200 µl 0.5× phosphate buffered saline (PBS) solution containing 115 ng of AOR and 43.4 nmoles NADPH, and incubated for 1 minute at 37° C. Reactions were then extracted with ethyl acetate containing piperine (internal standard), dried under vacuum, resuspended in HPLC buffer A (60% acetonitrile: 40% water), and injected into a Hewlett-Packard 1050 HPLC system equipped with a Luna $C_{18}$ column (Phenomenex Inc.). Metabolites were separated using buffer A at a flow rate of 1 ml/min and quantified using diode array detection at 205 nm and previously reported extinction coefficients (Tanaka, et al., 1990). $V_{max}$ and $K_m$ were calculated using the HYPER program. Illudin S was assayed in the same way with the following modifications: HPLC buffer B (35% acetonitrile: 5% methanol: 60% water), an umbelliferone internal standard, 38.3 ng of AOR, and a 2 minute incubation time were used. Irofulven was assayed in a similar fashion but with the following modifications: HPLC buffer C (40% acetonitrile: 60% water), a methyl pyridyl propanone internal standard, 2.3 µg AOR, and an 8 minute incubation time were used.

Identification of Metabolites. Large-scale reactions were completed for analysis of illudin M and irofulven metabolites by NMR and/or mass spectrometry. Ten mg of substrate were incubated with 66.7 mg of NADPH and 460 µg of AOR in 50 ml 0.5× PBS overnight at 37° C. Metabolites were extracted with ethyl acetate, dried under vacuum and purified using either flash chromatography or preparative TLC. 1H and 13C NMR analyses were completed on a Varian UNTY Plus 500-MHz NMR spectrometer. Electrospray-mass spectrometry was completed on a PR-Sciex API 150EX mass spectrometer.

Overexpression Studies. AOR-overexpressing 293 cells were produced and maintained as previously described (Dick, et al., 2001). Blank vector control, pCDP4, and overexpressing cells, pCEP4/AOR, were plated in 96-well plates at a density of 30,000 cells/well. Twenty-four h later, medium was replaced with serum-free medium containing the appropriate concentration of illudin M, irofulven, or metabolite dissolved in methanol. One to three serial dilutions were used to create the range of concentrations. Dicumarol was dissolved in 0.1 N NaOH and did not change the pH of the medium after addition. Cells wee incubated for 24 h, then viability was quantified using a methylthiazoletetrazolium-3-[4,5-dimethylthiazol-2-yl]-2,5-diphenyltetrazolium bromide] assay. A methanol-only control was used to determine viability.

Nonenzymatic Reactivity of Illudin M and Irofulven with GSH. Reaction of the 8,9-double bond with GSH was followed spectrophotometrically at 330 nm. At this wavelength illudin M and irofulven have significant absorbances due to conjugation of the 8,9 and 4,5-carbon-carbon double bonds with the ketone. Rearranged metabolites have no absorbance at this wavelength. GSH (3.25 mM) was added to 100 µM of either illudin M or irofulven in PBS (pH 7.4), and the reaction was monitored for 1 h at 30° C.

High Performance Liquid Chromatography with Tandem Mass Spectrometry (LC/MS/MS) of GSA Adducts. GSH adducts were prepared by adding 60 nmol of either illudin M or irofulven dissolved in acetonitrile to 200 ml of ammonium bicarbonate (pH 7.2) containing 1.8 µg AOR, 3.25 mM GSH and 0.6 mM NADPH. These reactions were incubated at 37° C. for 1 h. Controls lacking NAFPH were performed. Reactions were stopped and deproteinized with addition of 400 µl of ice-cold acetonitrile, spun at 3500×g for 10 min at 4° C., and the supernatants were evaporated to dryness under vacuum. Residual GSH and NADPH cofactors were removed using an Oasis $C_{18}$ sample prep column (Waters Chromatography). Adducts were eluted with methanol, evaporated to dryness under vacuum, resuspended in 250 ml of 0.1% acetic acid, and detected using liquid chromatography electrospray ionization tandem mass spectrometry performed in the positive ion mode. Samples were directly injected into a Finnigan MAT HPLC system equipped with a Luna $C_{18}$ column and coupled to a Finnigan LCQ detector. A flow rate of 0.1 ml/min and gradient of 0% buffer D (70% acetic acid (0.1%):30% acetonitrile) to 100% buffer E (20% acetic acid (0.1%):80% acetonitrile) over 30 min were used to resolve the compounds. Adducts were detected by monitoring for selected molecular ions or characteristic molecular fragments after MS/MS. Molecular fragments were obtained with 35% relative collusion energy.

EXAMPLES

While the following embodiments of the present invention have been described in detail, it is apparent that modifications and adaptations of those embodiments will occur to those of skill in the art. It is to be understood that such modifications and modifications are within the scope of the invention.

Example 1

Identification of Illudin and Irofulven Metabolites

Incubations of illudins M and S (FIG. 2, structures 1 and 2) with recombinant rat AOR in 0.5×PBS supplemented with NADPH leads to the formation of two metabolites each, as was previously reported (Tanaka, et al., 1990) following incubation with rat liver cytosol. Illudin M metabolites were purified from a larger scale reaction, subjected to analyses by $^1$H-NMR and ESI-MS, and determined to be identical to the previously reported metabolites (structures 3 and 4, and 5 and 6 in FIG. 2). Incubations of irofulven, (structure 7 in FIG. 2), with AOR leads to formation of only one metabolite, (structure 8 in FIG. 2) as reported previously (McMorris, et al., 1999). Similar analyses were used to confirm its identity.

Example 2

Kinetic Analysis of Illudin and Irofulven Metabolism by AOR

Three HLPC assays were used to measure the $V_{max}$ and $K_m$ of metabolism of illudins S and M, and irofulven. Rates were quantified from metabolite peak areas using reported extinction coefficients (Tanaka, et al., 1990; McMorris, et al., 1999). Illudins S and M are rapidly metabolized by AOR at rates exceeding those of any other substrate identified (Table 1). UV/visible wavelength spectra of all illudin metabolites were identical. Hydroxylation at the 15-position of illudin S appears to negatively effect binding to AOR, as evidenced by a higher $K_m$ than illudin M, but allows a slightly higher maximal rate. The aromaticity of the cyclopentane ring of irofulven is likely the cause of the 100-fold decrease in the rate of metabolism by AOR. However this modification does not seem to affect binding, as its $K_m$ is comparable to that of illudin M.

TABLE 1

| Substrate | Product | $V_{max}$(nmol/min/mg) | $K_m$(uM) |
|---|---|---|---|
| Irofulven | 8 | 275 | 145 |
| Illudin M | 3 | 29,200 | 109 |
|  | 4 | 14,900 | 113 |
| Illudin S | 5 | 65,400 | 486 |
|  | 6 | 50,500 | 308 |

Example 3

Effect of AOR Overexpression on Sensitivity of 293 Cells to Agents

Human embryonic kidney cells were transfected with either an episomal AOR overexpression vector (pCEP4/AOR) or a control vector (pCEP4). Transfected cells were then selected by addition of hygromycin to the growth media, producing a 25-fold increase in AOR activity over control cells. Percent viability was measured in cells seeded in 96-well plates using the 3-(4,5-dimethylthiazol-2-yl)-2,5-diphenyltetrazolium bromide assay 24-h after treatment with either irofulven, illudin M, or vehicle. Overexpression of AOR did not significantly affect illudin M cytotoxicity over a wide range of concentrations (FIG. 3A). The $LC_{50}$ (concentration required to produce 50 percent lethality) of this compound was measured to be approximately 1 μM, which is 2 orders of magnitude less than its $K_m$. Thus, illudin cytotoxicity is likely not dependent on reduction of the α,β-double bond by AOR.

Human 293 cells transfected with an AOR overexpression vector were 100-fold more sensitive than control cells to irofulven, but displayed little differential sensitivity to illudin M. Addition of glutathione to the alpha,beta-unsaturated ketone moiety of illudin M, but not irofulven, occurred readily at physiological concentrations. Electrophilic intermediates of irofulven and illudin M that were activated by AOR, were trapped with glutathione and identified by LC/MS/MS.

Overexpression of AOR dramatically (>100-fold) decreased the $LC_{50}$ of irofulven (FIG. 3B). This drastic change is likely due to the unmasking of the electrophilicity of the cyclopropyl group through metabolism by AOR. Activation was attenuated partially with addition of 100 μM dicumarol, an AOR inhibitor. This concentration of dicumarol alone was found to have no effect on cell growth. Inhibition of metabolically mediated cell death was not complete, presumably because of poor dicumarol solubility coupled with meager penetration of the cell membrane. The irofulven metabolite, (structure 8, FIG. 2) displayed no toxicity at concentrations up to 40 μM, ruling out the possibility that a combination of the metabolite and increased AOR levels is responsible for the change in cytotoxicity.

Example 4

Nonenzymatic Reductions of the 8,9-Double Bond with GSH

Figure 4:
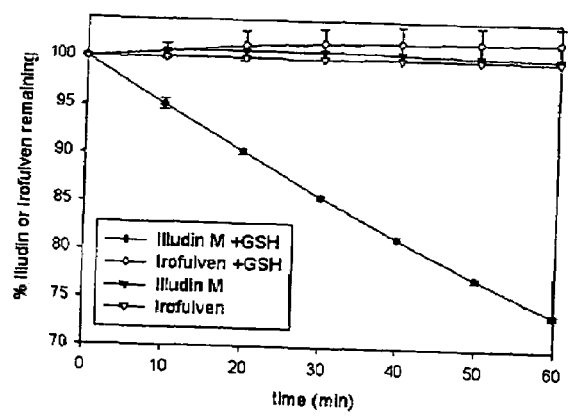
FIG. 4. Irofulven or illudin M were incubated with or without 3.25 mM reduced glutathione (GSH), and the presence of their 8,9-double bonds was monitored spectrophotometrically at 330 nm. Mean values (n=3) were plotted; bars, ±SD.

The sulfhydryl group of GSH is a potent nucleophile that rapidly reacts with most electrophilic α,β-unsaturated carbonyl groups via a Michael-addition mechanism. The reactivity of this moiety in the illudins and irofulven can be monitored spectrophotometrically by following a change inabsorbance at 330 nm, which is due to conjugation of the ketone with two or more carbon-carbon double bonds (McMorris, et al., 1965). Upon reduction of the α,β-bond and intramolecular rearrangement, this absorbance is lost, as evidenced by spectra of the metabolites. Incubations at physiologically relevant GSH concentrations and pH indicated that the α,β-unsaturated ketone of irofulven is relatively resistant to nucleophilic attack while that of illudin M is not (FIG. 4). These data, in conjunction with those gathered in the AOR overexpression experiments, support a mechanism of nonexzymatic attack of the α,β-double bond by cellular nucleophiles and subsequent macromolecular dysfunction.

Example 5

Mass Spectrometry of GSH Adducts

LC/MS/MS was used to further characterize pathways and consequences of enzymatic (E) and nonenzymatic (NE) reduction of the 8,9-double bonds of irofulven and illudin M (FIG. 1). Measuring GSH adduction is a commonly used technique for estimating covalent protein binding, and thus cytotoxicity, of a drug (Baillie and Kassahun, 2001). The nucleophilic thiol moiety of GSH effectively scavenges electrophilic molecules and its large size and charge prevent it from entering the active site of most enzymes. In the representative NE reaction (FIG. 1) illudin M is reduced by GSH at the α,β-double bond and, following rearrangement, a hydroxide ion adds to and opens the cyclopropyl ring. Thus, the net change to the molecular weight of the molecule is 307 m/z ($+GSH+OH-OH^-$). GSH adducts formed following enzymatically catalyzed hydride transfer (E) experience a net molecular weight change of 291 m/z ($+GSH+H^--OH^-$) and are thus easily distinguishable from the NE adducts. Daughter ions of adducts, which represent the loss of water (−18 m/z) or glutamine (−129 m/z), were common and monitored for in these experiments following MS/MS.

Figures 5A, 5B:
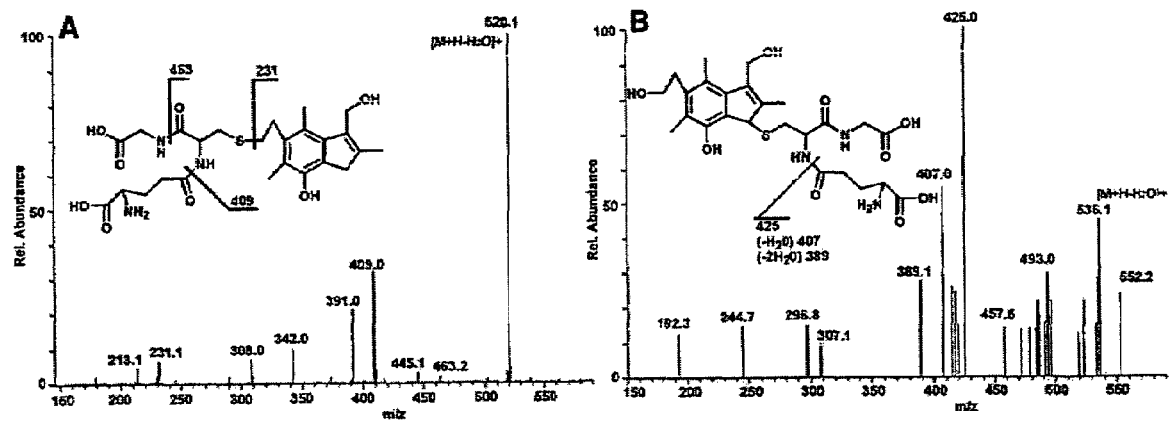
FIG. 5A. Irofulven was incubated with reduced glutathione (GSH) in the presence or absence of NADPH. Nonenzymatic (NE) and enzymatic (E) GSH adducts were detected and identified using high performance liquid chromatography with tandem mass spectrometry: irofulven (E).
FIG. 5B. Irofulven were incubated with reduced glutathione (GSH) in the presence or absence of NADPH. Nonenzymatic (NE) and enzymatic (E) GSH adducts were detected and identified using high performance liquid chromatography with tandem mass spectrometry: irofulven (NE).
Figures 5C, 5D:
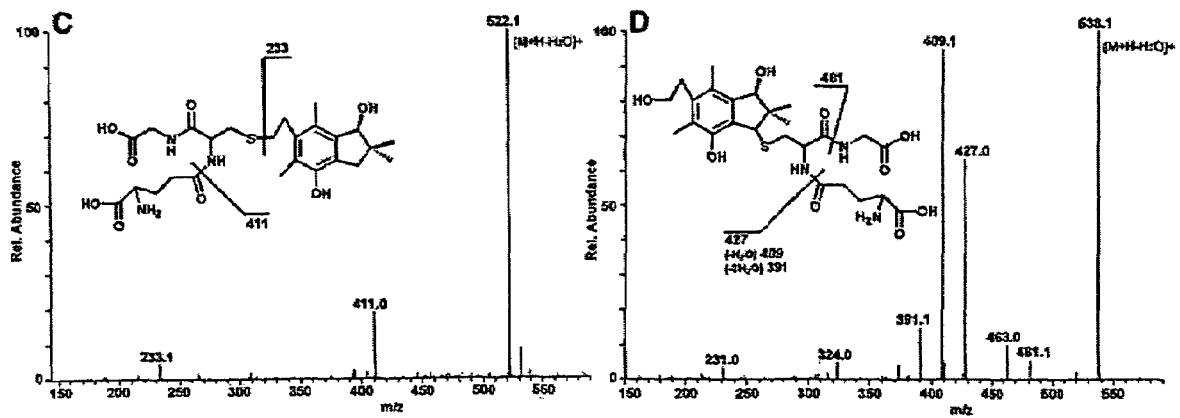
FIG. 5C. Illudin M was incubated with reduced glutathione (GSH) in the presence or absence of NADPH. Nonenzymatic (NE) and enzymatic (E) GSH adducts were detected and identified using high performance liquid chromatography with tandem mass spectrometry: illudin (E).
FIG. 5D. Illudin M was incubated with reduced glutathione (GSH) in the presence or absence of NADPH. Nonenzymatic (NE) and enzymatic (E) GSH adducts were detected and identified using high performance liquid chromatography with tandem mass spectrometry: irofulven (NE).

Irofulven and illudin GSH adducts were formed in vitro in incubations that favored enzymatic or nonenzymatic reduction of their 8,9-double bonds (FIG. 1). Enzymatic reduction occurred in incubations containing recombinant AOR, NADPH, and GSH, while companion nonenzymatic reductions lacked NADPH. Following a 1-h incubation at 37° C., samples were deproteinized and subjected to preliminary purification with Oasis $C_{18}$ sample prep columns. With addition of NADPH, the enzymatically reduced irofulven-GSH adduct (FIG. 5A) was easily detected when samples were monitored for the parent ion ($M^+$=538 m/z) or a specific daughter ion ($M^+-H_2O$=520 m/z). However the NE irofulven-GSH adduct (FIG. 5B) was detected only after monitoring for a daughter ion ($M+-H_2$=536 m/z) and was 42-fold less abundant than the E adduct. Similar amounts of NE irofulven-GSH adduct, and as expected no E adduct, were detected in NADPH-deficient samples. Surprisingly, the E illudin M-GSH adduct (FIG. 5C) was vastly (14-fold) predominant over the NE adduct (FIG. 5D) when incubations contained NADPH. This result indicates that AOR is capable of activating the illudins through metabolism; however, the AOR overexpression data show this route of activation is pharmacologically important. Contrary to findings with irofulven, a great deal of NE illudin M-GSH adduct was detected in NADPH-deficient incubations.

Example 6

Positive Association of Irofulven Sensitivity with AOR Activity Levels

To determine the significance of irofulven and illudin metabolism in a range of human cancers, a resource of the Developmental Therapeutics Program of the NCI was used. The NCI uses a panel of 60 human cancer cell lines to preliminarily evaluate potential chemotherapeutic agents. Sensitivity of cancers arising from nine different organs is estimated using five logarithmic concentrations of an agent and reported by concentration required to produce 50% lethality ($LD_{50}$), total growth inhibition, or growth inhibition of 50%.

Correlation of AOR Activity with Irofulven Sensitivity. Frozen cell pellets of 58 human tumor cell lines used by NCI to screen potential chemotherapeutic agents were obtained from the molecular targeteers program of the NCI. These pellets were thawed and resuspended in 400 µl PBS containing a mixture of mammalian protease inhibitors (Sigma). Cells were lysed by three freeze-thaw cycles, and centrifuged at 10,000×g for 1 h. Supernatants were then transferred to clean microfuge tubes and their protein content measured using BCA reagent (Pierce). AOR activities were measured using the illudin M HPLC assay described with the following changes: 20 µg of total protein, 60 nmol of illudin M, and 120 nmol of NADPH were dissolved in 200 µl of chloride-free 100 mM potassium phosphate buffer (pH 7.2). Reactions were incubated at 37° C. for 1 h and then stopped by addition of 300 µl of cold ethyl acetate containing curcumin as internal standard. Only hydroxylated metabolite peaks were detected and quantified. Activities were determined in triplicate and controls lacking NADPH were performed for each cell line. This assay was validated using a previously described chalcone assay to measure AOR activity in a random set of six cell lines (Dick, et al., 2001).

The AOR activities measured in cytosolic fractions prepared from each of the cell lines used irofulven as substrate and were analyzed by HPLC. AOR-specific activity was calculated and correlated to irofulven or illudin sensitivity using linear regression, as described. AOR activity measurements were verified in two ways; first, a random subset of cell lines was assayed using another AOR substrate, chalcone. Activity levels correlated nearly perfectly with those measured with irofulven; second, a Western blot of four cell lines that displayed a range of AOR activities was made using an anti-rat AOR primary antibody. Bands of the expected molecular weight were detected and their intensities correlated well with activities. Table 2 is list of cell lines and the AOR activities

TABLE 2

| type of cell line | name of line | activity (nmoles met/mg/min) | log activity met/min/mg |
| --- | --- | --- | --- |
| Non-Small Cell Lung | A549/ATCC | 6.2109 | 0.793157159 |
| Prostate | DU-145 | 4.2029 | 0.623545397 |
| Colon | HCC-2998 | 3.4891 | 0.542708749 |
| Non-Small Cell Lung | HOP-92 | 2.4362 | 0.386712567 |
| Non-Small Cell Lung | NCI-H460 | 2.4005 | 0.380305479 |
| Non-Small Cell Lung | HOP-62 | 2.3529 | 0.371596933 |
| Breast | T-47D | 2.0391 | 0.309430538 |
| Renal | 786-0 | 1.9271 | 0.284900495 |
| Non-Small Cell Lung | NCI-H226 | 1.6674 | 0.222052277 |
| Colon | COLO 205 | 1.5682 | 0.195409527 |
| Renal | UO-31 | 1.4932 | 0.174126464 |
| Ovarian | OVCAR-3 | 1.4396 | 0.15823681 |
| Renal | A498 | 1.3547 | 0.131839123 |
| Renal | TK-10 | 1.3253 | 0.122301227 |
| Non-Small Cell Lung | NCI-H23 | 1.2865 | 0.109395725 |
| Non-Small Cell Lung | NCI-H322M | 1.1805 | 0.072054495 |
| Central Nervous System | SF-539 | 1.1492 | 0.060402703 |
| Colon | HCT-116 | 1.1362 | 0.055453989 |
| Ovarian | IGROV1 | 1.1086 | 0.044772426 |
| Renal | SN12C | 1.0888 | 0.036948943 |
| Colon | HCT-15 | 1.0651 | 0.027392084 |
| Central Nervous System | SNB-75 | 1.0615 | 0.025902951 |
| Ovarian | OVCAR-8 | 1.0573 | 0.024194809 |
| Central Nervous System | SF-295 | 0.9026 | −0.04450267 |
| Central Nervous System | SF-268 | 0.8383 | −0.07661025 |
| Breast | MDA-MB-231/ATCC | 0.7281 | −0.13779406 |
| Ovarian | OVCAR-4 | 0.7091 | −0.14928358 |
| Ovarian | OVCAR-5 | 0.7039 | −0.15248518 |
| Renal | ACHN | 0.6979 | −0.15619643 |
| Ovarian | SK-OV-3 | 0.6750 | −0.17069623 |
| Renal | CAKI-1 | 0.6456 | −0.1900547 |
| Central Nervous System | SNB-19 | 0.5807 | −0.23602636 |
| Breast | NCI/ADR-RES | 0.5771 | −0.23876147 |
| Melanoma | UACC-257 | 0.5430 | −0.26522517 |
| Colon | HT29 | 0.5151 | −0.28810494 |
| Melanoma | MALME-3M | 0.4984 | −0.30238929 |
| Colon | KM12 | 0.4615 | −0.33586751 |
| Leukemia | HL-60(TB) | 0.4513 | −0.34553266 |
| Melanoma | SK-MEL-2 | 0.4503 | −0.34653623 |
| Prostate | PC-3 | 0.4404 | −0.35618762 |

TABLE 2-continued

| type of cell line | name of line | activity (nmoles met/mg/min) | log activity met/min/mg |
|---|---|---|---|
| Non-Small Cell Lung | EKVX | 0.4380 | −0.35850523 |
| Central Nervous System | U251 | 0.4372 | −0.35928053 |
| Melanoma | SK-MEL-28 | 0.4161 | −0.38075445 |
| Breast | HS 578T | 0.4135 | −0.38348073 |
| Melanoma | LOX IMVI | 0.4094 | −0.38787868 |
| Melanoma | M14 | 0.3753 | −0.42566724 |
| Non-Small Cell Lung | NCI-H522 | 0.3271 | −0.48534158 |
| Breast | MCF7 | 0.2487 | −0.60432785 |
| Melanoma | SK-MEL-5 | 0.2023 | −0.69391021 |
| Breast | MDA-MB-435 | 0.1781 | −0.74927512 |
| Leukemia | K-562 | 0.1719 | −0.76478729 |
| Colon | SW-620 | 0.1505 | −0.82240339 |
| Leukemia | RPMI-8226 | 0.0938 | −1.02802872 |
| Leukemia | MOLT-4 | 0.0901 | −1.04525513 |
| Leukemia | CCRF-CEM | 0.0617 | −1.20958288 |
| Leukemia | SR | 0.0359 | −1.44445214 |

Growth-inhibitory measures of irofulven sensitivity were obtained from data provided by the NCI. Logarithmic values of both sensitivity and AOR activity were plotted, and $R^2$ values were calculated using linear regression.

Table 3 shows log values for cell growth inhibition (TGI) and for 50% growth inhibition (GI50) in the presence of irofulven.

TABLE 3

| type of cell line | name of line | log(TGI) TGI | log(LC50) LC50 | log(GI50) GI50 |
|---|---|---|---|---|
| Leukemia | CCRF-CEM | −4.5 3.16E−05 | −4 1.00E−04 | −5.7 2.00E−06 |
| Leukemia | HL-60(TB) | −5.7 2.00E−06 | −4 1.00E−04 | −6.6 2.51E−07 |
| Leukemia | K-562 | −4 1.00E−04 | −4 1.00E−04 | −5.5 3.16E−06 |
| Leukemia | MOLT-4 | −4.7 2.00E−05 | −4 1.00E−04 | −6.1 7.94E−07 |
| Leukemia | RPMI-8226 | −4.1 7.94E−05 | −4 1.00E−04 | −4.5 3.16E−05 |
| Leukemia | SR | −4 1.00E−04 | −4 1.00E−04 | −6.1 7.94E−07 |
| Non-Small Cell Lung | A549/ATCC | −5.8 1.58E−06 | −4 1.00E−04 | −6.9 1.26E−07 |
| Non-Small Cell Lung | EKVX | −6.3 5.01E−07 | −5.4 3.98E−06 | −6.7 2.00E−07 |
| Non-Small Cell Lung | HOP-62 | −6.4 3.98E−07 | −5.9 1.26E−06 | −6.8 1.58E−07 |
| Non-Small Cell Lung | HOP-92 | −6.2 6.31E−07 | −4.6 2.51E−05 | −6.5 3.16E−07 |
| Non-Small Cell Lung | NCI-H226 | −6.3 5.01E−07 | −5.2 6.31E−06 | −6.7 2.00E−07 |
| Non-Small Cell Lung | NCI-H23 | −6.5 3.16E−07 | −6.1 7.94E−07 | −7.1 7.94E−08 |
| Non-Small Cell Lung | NCI-H322M | −6.2 6.31E−07 | −4.9 1.26E−05 | −6.6 2.51E−07 |
| Non-Small Cell Lung | NCI-H460 | −6.6 2.51E−07 |  | −7.3 5.01E−08 |
| Non-Small Cell Lung | NCI-H522 | −6.2 6.31E−07 | −5.1 7.94E−06 | −6.8 1.58E−07 |
| Colon | COLO 205 | −6.3 5.01E−07 | −6.2 6.31E−07 | −6.8 1.58E−07 |
| Colon | HCC-2998 | −6.5 3.16E−07 | −6.2 6.31E−07 | −6.8 1.58E−07 |
| Colon | HCT-116 | −6.3 5.01E−07 | −4.5 3.16E−05 | −6.7 2.00E−07 |
| Colon | HCT-15 | −5.3 5.01E−06 | −4 1.00E−04 | −6.5 3.16E−07 |
| Colon | HT29 | −5.9 1.26E−06 | −4 1.00E−04 | −6.6 2.51E−07 |
| Colon | KM12 | −5.6 2.51E−06 | −4.9 1.26E−05 | −6.2 6.31E−07 |
| Colon | SW-620 | −4.5 3.16E−05 | −4 1.00E−04 | −6.2 6.31E−07 |
| Central Nervous System | SF-268 | −5.6 2.51E−06 | −4 1.00E−04 | −6.6 2.51E−07 |
| Central Nervous System | SF-295 | −5.2 6.31E−06 | −5 1.00E−05 | −6.5 3.16E−07 |
| Central Nervous System | SF-539 | −6.3 5.01E−07 | −6.2 6.31E−07 | −6.8 1.58E−07 |
| Central Nervous System | SNB-19 | −5 1.00E−05 | −4.2 6.31E−05 | −6.5 3.16E−07 |
| Central Nervous System | SNB-75 | −6.3 5.01E−07 | −5.7 2.00E−06 | −6.7 2.00E−07 |
| Central Nervous System | U251 | −5.2 6.31E−06 | −4.3 5.01E−05 | −6.5 3.16E−07 |
| Melanoma | LOX IMVI | −5.5 3.16E−06 | −4.4 3.98E−05 | −6.2 6.31E−07 |
| Melanoma | MALME-3M | −6.3 5.01E−07 | −5.6 2.51E−06 | −6.7 2.00E−07 |
| Melanoma | M14 | −6.2 6.31E−07 | −5.7 2.00E−06 | −6.6 2.51E−07 |
| Melanoma | SK-MEL-2 | −6.4 3.98E−07 | −6.2 6.31E−07 | −6.7 2.00E−07 |
| Melanoma | SK-MEL-28 | −5.8 1.58E−06 | −4.7 2.00E−05 | −6.2 6.31E−07 |
| Melanoma | SK-MEL-5 | −6.4 3.98E−07 | −6 1.00E−06 | −6.8 1.58E−07 |
| Melanoma | UACC-257 | −6.3 5.01E−07 | −5.3 5.01E−06 | −6.6 2.51E−07 |
| Ovarian | IGROVI | −6.3 5.01E−07 | −5.2 6.31E−06 | −6.8 1.58E−07 |
| Ovarian | OVCAR-3 | −6.2 6.31E−07 | −4 1.00E−04 | −6.6 2.51E−07 |
| Ovarian | OVCAR-4 | −6.2 6.31E−07 | −4.6 2.51E−05 | −6.6 2.51E−07 |

TABLE 3-continued

| type of cell line | name of line | log(TGI) | TGI | log(LC50) | LC50 | log(GI50) | GI50 |
|---|---|---|---|---|---|---|---|
| Ovarian | OVCAR-5 | −6.3 | 5.01E−07 | −4.3 | 5.01E−05 | −6.8 | 1.58E−07 |
| Ovarian | OVCAR-8 | −6.2 | 6.31E−07 | −5 | 1.00E−05 | −6.7 | 2.00E−07 |
| Ovarian | SK-OV-3 | −6 | 1.00E−06 | −5 | 1.00E−05 | −6.6 | 2.51E−07 |
| Renal | 786-0 | −6.3 | 5.01E−07 | −5.7 | 2.00E−06 | −6.7 | 2.00E−07 |
| Renal | A498 | −6.3 | 5.01E−07 | −5.7 | 2.00E−06 | −6.7 | 2.00E−07 |
| Renal | ACHN | −6 | 1.00E−06 | −4 | 1.00E−04 | −6.6 | 2.51E−07 |
| Renal | CAKI-1 | −6.1 | 7.94E−07 | −4.3 | 5.01E−05 | −6.6 | 2.51E−07 |
| Renal | SN12C | −5.3 | 5.01E−06 | −4.3 | 5.01E−05 | −6.4 | 3.98E−07 |
| Renal | TK-10 | −5.9 | 1.26E−06 | −4 | 1.00E−04 | −6.6 | 2.51E−07 |
| Renal | UO-31 | −6.3 | 5.01E−07 | | | −6.7 | 2.00E−07 |
| Prostate | PC-3 | −5.9 | 1.26E−06 | −4.5 | 3.16E−05 | −6.6 | 2.51E−07 |
| Prostate | DU-145 | −6.7 | 2.00E−07 | −4 | 1.00E−04 | −7 | 1.00E−07 |
| Breast | MCF7 | −5.7 | 2.00E−06 | −4 | 1.00E−04 | −6.6 | 2.51E−07 |
| Breast | NCI/ADR-RES | −6.1 | 7.94E−07 | −5.3 | 5.01E−06 | −6.6 | 2.51E−07 |
| Breast | MDA-MB 231/ATCC | −5.9 | 1.26E−06 | −4.1 | 7.94E−05 | −6.5 | 3.16E−07 |
| Breast | HS 578T | −5.8 | 1.58E−06 | −4.7 | 2.00E−05 | −6.5 | 3.16E−07 |
| Breast | MDA-MB 435 | −5.2 | 6.31E−06 | −4.4 | 3.98E−05 | −5.8 | 1.58E−06 |
| Breast | T-47D | −5.6 | 2.51E−06 | −4 | 1.00E−04 | −6.7 | 2.00E−07 |

Samples of the 60-human tumor cell line panel used by the NCI to evaluate potential chemotherapeutic compounds were assayed for AOR activity (Table 2) correlated positively with the growth inhibitory measurements for irofulven. There was no correlation with growth inhibitory measurements for illudin M or illudin S.

Figure 6:
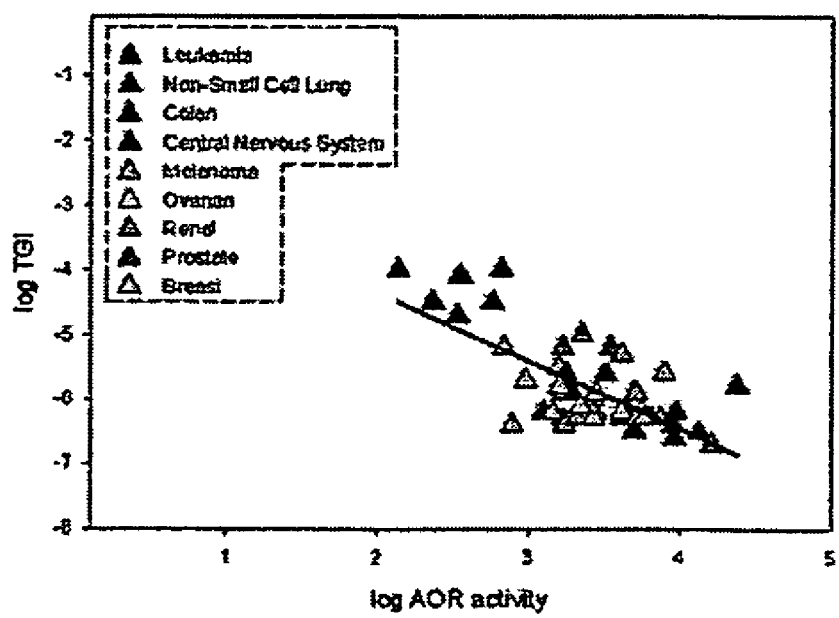
FIG. 6. Alkenal/one oxidoreductase (AOR) activity levels positively associate with irofulven sensitivity in human tumors. Samples of the cell lines used to evaluate potential anticancer agents were obtained from the National Cancer Institute (NCI), and AOR activity levels were measured in triplicate as described. Linear regression analysis gives R2=0.4929 (P<0.001).

As predicted from the overexpression experiments, AOR activity was not associated ($R^2 < 0.1$) with either measurement of illudin M or illudin S sensitivity. AOR activities, which varied by several orders of magnitude in this panel of cell lines, were positively associated with irofulven bioassays in terms of total growth inhibition (TGI) ($R^2 = 0.4929$, $p < 0.001$; FIG. 6) and growth inhibition of 50% ($R^2 = 0.4625$); however, maximal concentrations of irofulven used in the NCI assays were not sufficient for accurate estimation of the $LC_{50}$. Leukemic cell lines were relatively insensitive to irofulven and displayed the lowest AOR activities. Non-small cell lung cancer cell lines, on average, contained the highest levels of AOR activity and were the most sensitive to irofulven.

AOR has been detected at moderate levels in rat and human kidney (Yokomizo, et al., 1996); thus the high sensitivity of renal cancer cells was not unexpected. The highest levels of basal AOR expression are commonly found in the liver, however cell lines arising from this organ are not present in the NCI panel.

AOR has also proven very inducible by monofunctional inducers (e.g., 3H 1,2-dithiol-3-thione) in the rat and, as preliminary evidence suggests, bifunctional inducers (e.g., 3-methylcholanthrene) in the human. Thus AOR levels and consequently irofulven sensitivity can be influenced by diet and/or other drugs.

The following references, to the extent that they provide exemplary procedural or other details supplementary to those set forth herein, are specifically incorporated herein by reference.

REFERENCES

Baillie, T. A. and Kassahun, K. Biological reactive intermediate in drug discovery and development: a perspective from the pharmaceutical industry, Adv Exp Med Biol. 500: 45-51, 2001.

Bayes, M., Rabasseda, X., and Prous, J. R. Gateways to clinical trials. March 2003, Methods Find Exp Clin Pharmacol. 25: 145-68, 2003.

Britten, C. D., Hilsenbeck, S. G., Eckhardt, S. G., Marty, J., Mangold, G., MacDonald, J. R., Rowinsky, E. K., Von Hoff, D. D., and Weitman, S. Enhanced antitumor activity of 6-hydroxymethylacylfulvene in combination with irinotecan and 5-fluorouracil in the HT29 human colon tumor xenograft model, Cancer Res. 59: 1049-53, 1999.

Carmichael, J., DeGraff, W. G., Gazdar, A. F., Minna, J. D., and Mitchell, J. B. Evaluation of a tetrazolium-based semi-automated calorimetric assay: assessment of chemosensitivity testing, Cancer Res. 47: 93642, 1987

Dick, R. A., Kwak, M. K., Sutter, T. R., and Kensler, T. W. Antioxidative function and substrate specificity of NAD(P) H-dependent alkenal/one oxidoreductase. A new role for leukotriene $B_4$ 12-hydroxydehydrogenase/15oxoprostaglandin 13-reductase, J Biol Chem. 276: 40803-10, 2001.

Kelner, M. J., McMorris, T. C., Montoya, M. A., Estes, L., Rutherford, M., Samson, K. M., and Taetle, R. Characterization of cellular accumulation and toxicity of illudin S in sensitive and nonsensitive tumor cells, Cancer Chemother Pharmacol. 40: 65-71, 1997.

Kelner, M. J., McMorris, T. C., and Taetle, R. Pteclinical evaluation of illudins as anticancer agents: basis for selective cytotoxicity, J Natl Cancer Inst. 82: 1562-5, 1990.

Kelner; M: J., McMorris, T. C., Beck, W. T., Zamora, J. M., and Taetle, R. Preclinical evaluation of illudins as anticancer agents, Cancer Res. 47: 3186-9, 1987.

Leggas, M., Stewart, C. F., Woo, M. H., Fouladi, M., Cheshire, P. J., Peterson, J. K., Friedman, I-I. S., Billups, C., and Houghton, P. J. Relation between Irofulven (MGI-114) systemic exposure and tumor response in human solid tumor xenografts, Clin Cancer Res. 8: 3000-7, 2002.

MacDonald, J. R., Muscoplat, C. C., Dexter, D. L., Mangold, G. L., Chen, S. F., Kelner, M. J., McMorris; T. C., and Von. Hoff, D. D. Pre clinical antitumor activity of 6-hydroxymethylacylfulvene, a semisynthetic derivative of the mushroom toxin illudin S, Cancer Res. 57: 279-83, 1997.

McMorris, T. C., Kelner, M. J., Wang, W., Yu, J., Estes, L. A., and Taetle, R. (Hydroxymethyl)acylfulvene: an illudin derivative with superior antitumor properties; J: Nat Prod. 59 896-9., 1996.

McMorris, T. C. and Anchel, M. Fungal: Metabolites. The Structures of the Novel Sesquiterpenoids Illudin-S and -M, J. Am. Chem. Soc. 87: 1594-1600, 1965.

McMorris, T. C., Elayadi, A. N., Yu, J., Hu, Y., and Kelner, M. J. Metabolism of antitumor hydroxymethylacylfulvene by rat liver cytosol, Drug Metab Dispos. 27: 983-5, 1999.

McMorris, T. C., Kelner, M. J., Wang, W., Moon, S., and Taetle, R. On the mechanism of toxicity of illudins: the role of glutathione, Chem Res Toxicol. 3: 574-9, 1990.

Powis, G. Anticancer drugs: reactive metabolism and drug interactions, 1st edition, p. 444. Oxford, England: Pergamon Press, 1994.

Pratt, W. B. The anticancer drugs, 2nd edition, p. 352. New York: Oxford University Press, 1994.

Remington's Pharmaceutical Sciences, 15th Edition, Mack Publishing Co., 1975

Sato, Y., Kashimoto, S., MacDonald, J. R, and Nakano, K. In vivo antitumour efficacy of MGI-114 (6-hydroxymethylacylfulvene, HMAF) in various human tumour xenograft models including several lung and gastric tumours, Eur J Cancer. 37: 1419-28, 2001.

Tanaka, K., Inoue, T., Kadota, S., and Kikuchi, T. Metabolism of illudin S, a toxic principle of Lampteromyces japonicus, by rat liver. 1. Isolation and identification of cyclopropane ring-cleavage metabolites, Xenobiotica. 20: 671-681, 1990.

Tanaka, K., Inoue, T., Kadota, S., and Kikuchi, T. Metabolism by rat liver cytosol of illudin S, a toxic substance of Lampteromyces japonicus; II. Characterization of illudin S-metabolizing enzymes Xenobiotica. 22: 33-39, 1992.

Yokomizo, T., Ogawa, Y., Uozumi, N., Kume, K., Izumi, T., and Shimizu, T. cDNA cloning, expression, and mutagenesis study of leukotriene $B_4$ hydroxydehydrogenase, J Biol Chem 271: 2844-50, 1996.

U.S. Pat. No. 6,025,328;
U.S. Pat. No. 5,932,553; U.S.
U.S. Pat. No. 6,548,679

SEQ. ID NO: 1

Rat AOR protein sequence:

```
  1 mvqaktwtlk khfegfptds nfelrttelp plnngevlle alflsvdpym rvaakklkeg 61 dsmmgeqvar vvesknsafp tgtivvallg wtshsisdgn glrklpaewp dklplslalg 121 tvgmpgltay fglldicglk ggetvlvnaa agavgsvvgq iaklkgckvv gtagsdekva 181 ylkklgfdva fnyktvksle ealrtaspdg ydcyfdnvgg efsntvilqm ktfgriaicg 241 aisqynrtgp cppgpspevi iyqqlrmegf ivtrwqgevr qkaltdlmnw vsegkiryhe 301 yitegfekmp aafmgmlkgd nlgktivka
```

---

Rat AOR cDNA sequence:

```
  1 atggtacaag ctaagacctg gacccctaaag aagcactttg aaggcttccc tacggacagt    SEQ. ID NO: 2

61 aactttgagt tgaggacgac tgagctccca cccttaaata atggagaggt cctgctgaa 121 gccctgttcc tctccgtgga cccttacatg agagttgcag caaaaaaact gaaggagggc 181 gacagcatga tgggtgaaca agtggccaga gttgtggaaa gtaaaaactc agccttccca 241 acgggaacga ttgttgtggc tttattaggt tggacatcac attccatttc tgatgggaat 301 ggactgagaa agctacctgc agagtggcct gacaagctac cactgtctttt ggctttgggg 361 acagttggca tgccaggcct cactgcctac tttggcctgc ttgacatctg tggcttgaag 421 ggtggagaaa cagtgctggt caatgcggca gccggggctg tgggctctgt tgtggggcag 481 atagctaagc tcaagggctg caaagttgtt ggtacagccg gtctgatga aaaggttgcc 541 tatcttaaga gcttggatt cgatgtggcc tttaactaca gacagtaaa gtcattggaa 601 gaagcttga ggacagcctc tccagatggt tatgattgct acttttgataa tgtcggtgga 661 gagttttcaa acactgttat actgcagatg aagacgtttg gaagaattgc catctgtggc 721 gccatctctc aatacaaccg cactggccca tgtcccccag gcccatctcc agaggtcatt
```

-continued

Rat AOR cDNA sequence:

```
781 atctatcagc aactccgcat ggaggggttc atcgttactc ggtggcaagg agaagtccgc
841 cagaaggctc tgacagactt gatgaattgg gtttcagagg gtaagatccg gtatcatgaa
901 tacatcactg aaggatttga agatgcccc gcagcgttca tgggaatgtt gaaaggagac
961 aatctgggga agactatagt gaaagcgtga
```

Human AOR protein sequence:

```
1   mvrtktwtlk khfvgyptns dfelktselp plkngevlle alfltvdpym rvaakrlkeg      SEQ. ID NO: 3
61  dtmmgqqvak vvesknvalp kgtivlaspg wtthsisdgk dleklltewp dtiplslalg
121 tvgmpgltay fglleicgvk ggetvmvnaa agavgsvvgq iaklkgckvv gavgsdekva
181 ylqklgfdvv fnyktvesle etlkkaspdg ydcyfdnvgg efsntvigqm kkfgriaicg
241 aistynrtgp lppgpppeiv iyqelrmeaf vvyrwqgdar qkalkdllkw vlegkiqyke
301 yiiegfenmp aafmgmlkgd nlgktivka
```

Human AOR mRNA sequence (underlined is Human AOR cDNA):

```
1    gtcccgacgc ctcccgcccc cgcagttcct tggagagctt ggagccgcgc gccgaggga       SEQ. ID NO: 4
61   ataggaaagc ttggttacaa cccgggacac ccggagcttc agg atggttc gtactaagac
121  atggaccctg aagaagcact tgttggcta tcctactaat agtgactttg agttgaagac
181  atctgagctc ccaccccttaa aaaatggaga ggtcctgctt gaagctttgt tcctcaccgt
241  ggatccctac atgagagtgg cagccaaaag attgaaggaa ggtgatacaa tgatgggca
301  gcaagtggcc aaagttgtgg aaagtaaaaa tgtagcccta ccaaaaggaa ctattgtact
361  ggcttctcca ggctggacaa cgcactccat ttctgatggg aaagatctgg aaaagctgct
421  gacagagtgg ccagacacaa taccactgtc tttggctctg ggacagttg gcatgccagg
481  cctgactgcc tactttggcc tacttgaaat ctgtggtgtg aagggtggag aaacagtgat
541  ggttaatgca gcagctggag ctgtgggctc agtcgtgggg cagattgcaa agctcaaggg
601  ctgcaaagtt gttggagcag tagggtctga tgaaaaggtt gcctaccttc aaaagcttgg
661  atttgatgtc gtctttaact acaagacggt agagtctttg gaagaaacct tgaagaaagc
721  gtctcctgat ggttatgatt gttattttga taatgtaggg ggagagtttt caaacactgt
781  tatcggccag atgaagaaat ttggaaggat tgccatatgt ggagccatct ctacatataa
841  cagaaccggc ccacttcccc caggcccacc cccagagatt gttatctatc aggagcttcg
901  catggaagct tttgtcgtct accgctggca aggagatgcc cgccaaaaag ctctgaagga
961  cttgctgaaa tgggtcttag agggtaaaat ccagtacaag gaatatatca ttgaaggatt
1021 tgaaaacatg ccagccgcat ttatgggaat gctgaaagga gataatttgg ggaagacaat
1081 agtgaaagca tgaaaaagag gacacatgga atctggaggc catttagatg attagttaat
1141 ttgttttttca ccatttagca aaaatgtata ctaccttaaa tgtcttaaga aatagtactc
1201 ataatgagtt tgagctactt aataaaatac atttaagtgg taaaaaaaaa aaaaaaa
```

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An in vitro method of assessing cancer cell toxicity of an acylfulvene candidate drug, wherein the cancer cell is selected from leukemia, non-small cell lung, colon, central nervous system, melanoma, ovarian, renal, prostate and breast cancer cells, and wherein the cancer cells expresses NADPH alkenal/one oxidoreductase (AOR), comprising: incubating the candidate drug with a medium chain reductase that reduces an α,β-unsaturated aldehyde/ketone fulvene at ring position 8,9 of the candidate drug, wherein the medium chain reductase is a polypeptide having the amino acid sequence of SEQ ID NO: 1, SEQ ID NO:3 or an amino acid sequence at least 95% identical thereto; determining a reduction rate for said candidate drug; and comparing said rate with a model substrate reduction rate; wherein a reduction rate for the candidate drug less than the reduction rate for the model substrate is predictive of increased cancer cell toxicity of the candidate acylfulvene drug compared with the model substrate, and wherein the model substrate is irofulvin.

2. The method of claim 1 wherein the medium chain reductase is encoded by a nucleic acid having the sequence of SEQ ID NO: 2, SEQ ID NO:4 or variants thereof that encode the polypeptides set forth as SEQ ID NO 1 or SEQ ID NO: 3.

3. The method of claim 1, wherein the reduction rate is a maximum reduction rate (Vmax).

4. The method of claim 1 wherein the reduction rate is a specific activity rate.

5. The method of claim 3, wherein the Vmax of the candidate acylfulvene drug has a Vmax equal to or less than the Vmax of irofulven.

6. The method of claim 1 further comprising measuring double bond stability toward reduction by incubating the candidate acylfulvene drug with a nucleophile.

7. The method of claim 6, wherein the nucleophile is glutathione.

8. An in vitro method of assessing cancer cell toxicity of an acylfulvene candidate drug, wherein the cancer coil is in vitro and is selected from leukemia, non-small cell lung, colon, central nervous system, melanoma, ovarian, renal, prostate and breast cancer cells, and wherein the cancer cell expresses NADPH alkenal/one oxidoreductase (AOR), comprising: incubating the candidate drug with a medium chain reductase that reduces an α,β-unsaturated aldehyde/ketone fulvene at ring position 8,9 of the candidate drug, wherein the medium chain reductase is a polypeptide having the amino acid sequence of SEQ ID NO: 1, SEQ ID NO:3 or an amino acid sequence at least 95% identical thereto; determining a reduction rate for said candidate drug; and comparing said rate with a model substrate reduction rate; wherein a reduction rate for the candidate drug less than the reduction rate for the model substrate is predictive of increased cancer cell toxicity of the candidate acylfulvene drug compared with the model substrate, and wherein the model substrate is selected from illudin M, illudin S or irofulvin.

9. The method of claim 8, wherein the reduction rate is a maximum reduction rate (Vmax).

10. The method of claim 9, wherein the Vmax of the candidate acylfulvene drug has a Vmax equal to or less than the Vmax of irofulven.

11. The method of claim 9, wherein the Vmax of the candidate acylfulvene drug has a Vmax of about one order of magnitude less than the Vmax of illudin M.

12. The method of claim 9, wherein the Vmax of the candidate acylfulvene drug has a Vmax about two orders of magnitude less than the Vmax of illudin S.

* * * * *

UNITED STATES PATENT AND TRADEMARK OFFICE
CERTIFICATE OF CORRECTION

PATENT NO. : 7,718,385 B2
APPLICATION NO. : 10/968727
DATED : May 18, 2010
INVENTOR(S) : Ryan A. Dick Page 1 of 1

It is certified that error appears in the above-identified patent and that said Letters Patent is hereby corrected as shown below:

Col. 34, Line 16,
Claim 8 should read:

8. An in vitro method of assessing cancer cell toxicity of an acylfulvene candidate drug, wherein the cancer ~~coil~~ <u>cell</u> is in vitro and is selected from leukemia, non-small cell lung, colon, central nervous system, melanoma, ovarian, renal, prostate and breast cancer cells, and wherein the cancer cell expresses NADPH alkenal/one oxidoreductase (AOR), comprising: incubating the candidate drug with a medium chain reductase that reduces an α,β-unsaturated aldehyde/ketone fulvene at ring position 8,9 of the candidate drug, wherein the medium chain reductase is a polypeptide having the amino acid sequence of SEQ ID NO: 1, SEQ ID NO:3 or an amino acid sequence at least 95% identical thereto; determining a reduction rate for said candidate drug; and comparing said rate for the candidate drug less than the reduction rate for the model substrate is predictive of increased cancer cell toxicity of the candidate acylfulvene drug compared with the model substrate, and wherein the model substrate is selected from illudin M, illudin S or irofulvin.

Signed and Sealed this

Seventh Day of September, 2010

David J. Kappos
*Director of the United States Patent and Trademark Office*

SEQUENCE LISTING

<160> NUMBER OF SEQ ID NOS: 4

<210> SEQ ID NO 1
<211> LENGTH: 329
<212> TYPE: PRT
<213> ORGANISM: Rattus norvegicus

<400> SEQUENCE: 1

Met Val Gln Ala Lys Thr Trp Thr Leu Lys Lys His Phe Glu Gly Phe
 1               5                  10                  15

Pro Thr Asp Ser Asn Phe Glu Leu Arg Thr Thr Glu Leu Pro Pro Leu
             20                  25                  30

Asn Asn Gly Glu Val Leu Leu Glu Ala Leu Phe Leu Ser Val Asp Pro
         35                  40                  45

Tyr Met Arg Val Ala Ala Lys Lys Leu Lys Glu Gly Asp Ser Met Met
     50                  55                  60

Gly Glu Gln Val Ala Arg Val Val Glu Ser Lys Asn Ser Ala Phe Pro
 65                  70                  75                  80

Thr Gly Thr Ile Val Val Ala Leu Leu Gly Trp Thr Ser His Ser Ile
                 85                  90                  95

Ser Asp Gly Asn Gly Leu Arg Lys Leu Pro Ala Glu Trp Pro Asp Lys
            100                 105                 110

Leu Pro Leu Ser Leu Ala Leu Gly Thr Val Gly Met Pro Gly Leu Thr
        115                 120                 125

Ala Tyr Phe Gly Leu Leu Asp Ile Cys Gly Leu Lys Gly Gly Glu Thr
    130                 135                 140

Val Leu Val Asn Ala Ala Ala Gly Ala Val Gly Ser Val Val Gly Gly
145                 150                 155                 160

Ile Ala Lys Leu Lys Gly Cys Lys Val Val Gly Thr Ala Gly Ser Asp
                165                 170                 175

Glu Lys Val Ala Tyr Leu Lys Lys Leu Gly Phe Asp Val Ala Phe Asn
            180                 185                 190

Tyr Lys Thr Val Lys Ser Leu Glu Glu Ala Leu Arg Thr Ala Ser Pro
        195                 200                 205

Asp Gly Tyr Asp Cys Tyr Phe Asp Asn Val Gly Gly Glu Phe Ser Asn
    210                 215                 220

Thr Val Ile Leu Gln Met Lys Thr Phe Gly Arg Ile Ala Ile Cys Gly
225                 230                 235                 240

Ala Ile Ser Gln Tyr Asn Arg Thr Gly Pro Cys Pro Pro Gly Pro Ser
                245                 250                 255

Pro Glu Val Ile Ile Tyr Gly Gly Leu Arg Met Glu Gly Phe Ile Val
            260                 265                 270

Thr Arg Trp Gly Gly Glu Val Arg Gln Lys Ala Leu Thr Asp Leu Met
        275                 280                 285

Asn Trp Val Ser Glu Gly Lys Ile Arg Tyr His Glu Tyr Ile Thr Glu
    290                 295                 300

```
Gly Phe Glu Lys Met Pro Ala Ala Phe Met Gly Met Leu Lys Gly Asp
305                 310                 315                 320

Asn Leu Gly Lys Thr Ile Val Lys Ala
                325
```

<210> SEQ ID NO 2
<211> LENGTH: 990
<212> TYPE: DNA
<213> ORGANISM: Rattus norvegicus

<400> SEQUENCE: 2

| | | | | | |
|---|---|---|---|---|---|
| atggtacaag | ctaagacctg | accctaaag | aagcactttg | aaggcttccc | tacggacagt | 60 |
| aactttgagt | tgaggacgac | tgagctccca | cccttaaata | atggagaggt | cctgctggaa | 120 |
| gccctgttcc | tctccgtgga | cccttacatg | agagttgcag | caaaaaaact | gaaggagggc | 180 |
| gacagcatga | tgggtgaaca | agtggccaga | gttgtggaaa | gtaaaaactc | agccttccca | 240 |
| acgggaacga | ttgttgtggc | tttattaggt | tggacatcac | attccatttc | tgatgggaat | 300 |
| ggactgagaa | agctacctgc | agagtggcct | gacaagctac | cactgtcttt | ggctttgggg | 360 |
| acagttggca | tgccaggcct | cactgcctac | tttggcctgc | ttgacatctg | tggcttgaag | 420 |
| ggtggagaaa | cagtgctggt | caatgcggca | gccggggctg | tgggctctgt | tgtggggcag | 480 |
| atagctaagc | tcaagggctg | caaagttgtt | ggtacagccg | ggtctgatga | aaaggttgcc | 540 |
| tatcttaaga | gcttggatt | cgatgtggcc | tttaactaca | agacagtaaa | gtcattggaa | 600 |
| gaagctttga | ggacagcctc | tccagatggt | tatgattgct | actttgataa | tgtcggtgga | 660 |
| gagttttcaa | acactgttat | actgcagatg | aagacgtttg | aagaattgc | catctgtggc | 720 |
| gccatctctc | aatacaaccg | cactggccca | tgtcccccag | gcccatctcc | agaggtcatt | 780 |
| atctatcagc | aactccgcat | ggaggggttc | atcgttactc | ggtggcaagg | agaagtccgc | 840 |
| cagaaggctc | tgacagactt | gatgaattgg | gtttcagagg | gtaagatccg | gtatcatgaa | 900 |
| tacatcactg | aaggatttga | aagatgccc | gcagcgttca | tgggaatgtt | gaaaggagac | 960 |
| aatctgggga | agactatagt | gaaagcgtga | | | | 990 |

<210> SEQ ID NO 3
<211> LENGTH: 329
<212> TYPE: PRT
<213> ORGANISM: Homo sapiens

<400> SEQUENCE: 3

```
Met Val Arg Thr Lys Thr Trp Thr Leu Lys Lys His Phe Val Gly Tyr
 1               5                  10                  15

Pro Thr Asn Ser Asp Phe Glu Leu Lys Thr Ser Glu Leu Pro Pro Leu
            20                  25                  30

Lys Asn Gly Glu Val Leu Leu Glu Ala Leu Phe Leu Thr Val Asp Pro
        35                  40                  45

Tyr Met Arg Val Ala Ala Lys Arg Leu Lys Glu Gly Asp Thr Met Met
    50                  55                  60

Gly Gln Gln Val Ala Lys Val Val Glu Ser Lys Asn Val Ala Leu Pro
65                  70                  75                  80

Lys Gly Thr Ile Val Leu Ala Ser Pro Gly Trp Thr Thr His Ser Ile
                85                  90                  95

Ser Asp Gly Lys Asp Leu Glu Lys Leu Leu Thr Glu Trp Pro Asp Thr
            100                 105                 110

Ile Pro Leu Ser Leu Ala Leu Gly Thr Val Gly Met Pro Gly Leu Thr
        115                 120                 125
```

```
Ala Tyr Phe Gly Leu Leu Glu Ile Cys Gly Val Lys Gly Gly Glu Thr
            130                 135                 140
Val Met Val Asn Ala Ala Gly Ala Val Gly Ser Val Val Gly Gln
145                 150                 155                 160
Ile Ala Lys Leu Lys Gly Cys Lys Val Val Gly Ala Val Gly Ser Asp
                165                 170                 175
Glu Lys Val Ala Tyr Leu Gln Lys Leu Gly Phe Asp Val Val Phe Asn
                180                 185                 190
Tyr Lys Thr Val Glu Ser Leu Glu Glu Thr Leu Lys Lys Ala Ser Pro
            195                 200                 205
Asp Gly Tyr Asp Cys Tyr Phe Asp Asn Val Gly Gly Glu Phe Ser Asn
            210                 215                 220
Thr Val Ile Gly Gln Met Lys Lys Phe Gly Arg Ile Ala Ile Cys Gly
225                 230                 235                 240
Ala Ile Ser Thr Tyr Asn Arg Thr Gly Pro Leu Pro Pro Gly Pro Pro
                245                 250                 255
Pro Glu Ile Val Ile Tyr Gln Glu Leu Arg Met Glu Ala Phe Val Val
                260                 265                 270
Tyr Arg Trp Gln Gly Asp Ala Arg Gln Lys Ala Leu Lys Asp Leu Leu
            275                 280                 285
Lys Trp Val Leu Glu Gly Lys Ile Gln Tyr Lys Glu Tyr Ile Ile Glu
            290                 295                 300
Gly Phe Glu Asn Met Pro Ala Ala Phe Met Gly Met Leu Lys Gly Asp
305                 310                 315                 320
Asn Leu Gly Lys Thr Ile Val Lys Ala
                325

<210> SEQ ID NO 4
<211> LENGTH: 1257
<212> TYPE: DNA
<213> ORGANISM: Homo sapiens

<400> SEQUENCE: 4
gtcccgacgc ctcccgcccc cgcagttcct tggagagctt ggagccgcgc gccggaggga    60
ataggaaagc ttggttacaa cccgggacac ccggagcttc aggatggttc gtactaagac   120
atggaccctg aagaagcact tgttggcta tcctactaat agtgactttg agttgaagac   180
atctgagctc ccacccttaa aaatggaga ggtcctgctt gaagctttgt tcctcaccgt   240
ggatccctac atgagagtgg cagccaaaag attgaaggaa ggtgatacaa tgatggggca   300
gcaagtggcc aaagttgtgg aaagtaaaaa tgtagcccta ccaaaaggaa ctattgtact   360
ggcttctcca ggctggacaa cgcactccat ttctgatggg aaagatctgg aaaagctgct   420
gacagagtgg ccagacacaa taccactgtc tttggctctg ggacagttg gcatgccagg   480
cctgactgcc tactttggcc tacttgaaat ctgtggtgtg aagggtggag aaacagtgat   540
ggttaatgca gcagctggag ctgtgggctc agtcgtgggg cagattgcaa agctcaaggg   600
ctgcaaagtt gttggagcag tagggtctga tgaaaaggtt gcctaccttc aaaagcttgg   660
atttgatgtc gtctttaact acaagacggt agagtctttg gaagaaacct tgaagaaagc   720
gtctcctgat ggttatgatt gttatttga taatgtaggt ggagagtttt caaacactgt   780
tatcggccag atgaagaaat ttggaaggat tgccatatgt ggagccatct ctacatataa   840
cagaaccggc ccacttcccc caggcccacc cccagagatt gttatctatc aggagcttcg   900
catggaagct tttgtcgtct accgctggca aggagatgcc cgccaaaaag ctctgaagga   960
```

| | | | | |
|---|---|---|---|---|
| cttgctgaaa | tgggtcttag | agggtaaaat | ccagtacaag | gaatatatca ttgaaggatt | 1020 |
| tgaaaacatg | ccagccgcat | ttatgggaat | gctgaaagga | gataatttgg ggaagacaat | 1080 |
| agtgaaagca | tgaaaaagag | gacacatgga | atctggaggc | catttagatg attagttaat | 1140 |
| ttgtttttca | ccatttagca | aaaatgtata | ctaccttaaa | tgtcttaaga aatagtactc | 1200 |
| ataatgagtt | tgagctactt | aataaaatac | atttaagtgg | taaaaaaaaa aaaaaaa | 1257 |